US012678336B2

(12) United States Patent
Hu et al.

(10) Patent No.: US 12,678,336 B2
(45) Date of Patent: Jul. 14, 2026

(54) HYDRATION-RESPONSIVE SHAPE-MEMORY KERATIN COMPOSITE FIBERS AND FABRICATION METHODS THEREOF

(71) Applicant: City University of Hong Kong, Hong Kong (HK)

(72) Inventors: Jinlian Hu, Hong Kong (HK); Xiaoyun Xu, Hong Kong (HK)

(73) Assignee: City University of Hong Kong, Hong Kong (HK)

( * ) Notice: Subject to any disclaimer, the term of this patent is extended or adjusted under 35 U.S.C. 154(b) by 25 days.

(21) Appl. No.: 18/770,691

(22) Filed: Jul. 12, 2024

(65) Prior Publication Data

US 2025/0041123 A1     Feb. 6, 2025

Related U.S. Application Data

(60) Provisional application No. 63/517,605, filed on Aug. 3, 2023.

(51) Int. Cl.
*F03G 7/06* (2006.01)
*A61F 13/01* (2024.01)
(Continued)

(52) U.S. Cl.
CPC .. *A61F 13/01012* (2024.01); *A61F 13/01038* (2024.01); *A61F 13/01042* (2024.01); *A61L 15/28* (2013.01); *A61L 15/32* (2013.01); *A61L 15/42* (2013.01); *D01D 5/06* (2013.01); *D01F 1/10* (2013.01); *D01F 4/00* (2013.01); *D01F 11/02* (2013.01); *F03G 7/0614* (2021.08);
(Continued)

(58) Field of Classification Search
None
See application file for complete search history.

(56) References Cited

U.S. PATENT DOCUMENTS

| | | | |
|---|---|---|---|
| 11,939,704 B2 * | 3/2024 | Hu | D02G 3/28 |
| 2020/0362474 A1 * | 11/2020 | Liukkonen | B23K 26/0846 |
| 2025/0019867 A1 * | 1/2025 | Breslauer | D01F 8/02 |

FOREIGN PATENT DOCUMENTS

| | | | |
|---|---|---|---|
| CN | 102839441 B | | 10/2014 |
| CN | 111910282 B | | 3/2022 |
| JP | 2000008233 A | * | 1/2000 |

OTHER PUBLICATIONS

Xueling Xio, Jinlian Hu, Xiaoting Gui, Kun Qiam, Shape Memory Investigation of α-Keratin Fibers as Multi-Coupled Stimuli of Responsive Smart Material, Polymers, Mar. 3, 2017 9(3):87 DOI:3390/ polym9030087 https://pmc.ncbi.nlm.nih.gov/articles/PMC6432327/ (Year: 2017).*

(Continued)

*Primary Examiner* — Kim M Lewis

(74) *Attorney, Agent, or Firm* — Idea Intellectual Limited; Sam T. Yip

(57) ABSTRACT

Hydration-responsive shape-memory keratin composite fibers are provided. These fibers have a keratin network structure formed by keratin α-helices bonded by disulfide bonds. Incorporated within the structure are cellulose nanocrystals (CNCs), which provide hydrogen bonds and stabilize the α-helix structure, introducing a hydration-responsive switch. Specifically, the CNCs are configured to arrange and connect the keratin α-helices, aligning their coil axis along the fiber axis.

6 Claims, 24 Drawing Sheets

(51) Int. Cl.

| | |
|---|---|
| *A61L 15/28* | (2006.01) |
| *A61L 15/32* | (2006.01) |
| *A61L 15/42* | (2006.01) |
| *D01D 5/06* | (2006.01) |
| *D01F 1/10* | (2006.01) |
| *D01F 4/00* | (2006.01) |
| *D01F 11/02* | (2006.01) |

(52) U.S. Cl.
CPC ....... *A61L 2400/04* (2013.01); *A61L 2400/12* (2013.01); *A61L 2400/16* (2013.01); *D10B 2211/01* (2013.01); *D10B 2401/02* (2013.01); *D10B 2505/00* (2013.01); *D10B 2509/022* (2013.01)

(56) References Cited

OTHER PUBLICATIONS

Tarah N. Sullivan et al., "Hydration-Induced Shape and Strength Recovery of the Feather", Advanced Functional Materials, 2018, vol. 28, No. 1801250, p. 1-9.

Xueliang Xiao et al., "Animal Hairs as Water-stimulated Shape Memory Materials: Mechanism and Structural Networks in Molecular Assemblies", Scientific Reports, 2016, vol. 6, No. 26393, p. 1-12.

Xueliang Xiao et al., "Is biopolymer hair a multi-responsive smart material?", Polymer Chemistry, 2017, vol. 8, p. 283-294.

Xueliang Xiao et al., "Shape Memory Investigation of α-Keratin Fibers as Multi-Coupled Stimuli of Responsive Smart Materials", Polymers, 2017, vol. 9, No. 87, p. 1-15.

Yi Xi Song et al., "Improvement of multiple-responsive shape memory effects of wool through increasing the content of disulfide bonds", Polymer, 2020, vol. 188, No. 122130, p. 1-9.

Luca Cera et al., "A bioinspired and hierarchically structured shape-memory material", Nature Materials, 2021, vol. 20, p. 242-249.

Yanting Han et al., "Achieving coalesced breathability, mechanical and shape memory properties of collagen fibrous matrix through complexing with chromium (III)", Materials and Design, 2020, vol. 186, No. 108206, p. 1-10.

Yanting Han et al., "Collagen skin, a water-sensitive shape memory material", Journal of Materials Chemistry B, 2018, vol. 6, p. 5144-5152.

Yanting Han et al., "Tea-polyphenol treated skin collagen owns coalesced adaptive-hydration, tensile strength and shape-memory property", International Journal of Biological Macromolecules, 2020, vol. 158, p. 1-8.

Fang Chen et al., "Thermal- and salt-activated shape memory hydrogels based on a gelatin/polyacrylamide double network", RSC Advances, 2019, vol. 9, p. 18619-18626.

Xueqi Leng et al., "Tuning the reversibility of hair artificial muscles by disulfide cross-linking for sensors, switches, and soft robotics", Materials Horizons, 2021, vol. 8, p. 1538-1546.

Ke Li et al., "Wet-Driven Bionic Actuators from Wool Artificial Yarn Muscles", ACS Applied Materials & Interfaces, 2023, vol. 15, p. 16232-16243.

Kaili Song et al., "Keratin-Based Biocomposites Reinforced and Cross-Linked with Dual-Functional Cellulose Nanocrystals", ACS Sustainable Chemistry & Engineering, 2017, vol. 5, p. 5669-5678.

Guangsheng Cao et al., "Continuous High-Content Keratin Fibers with Balanced Properties Derived from Wool Waste", ACS Sustainable Chemistry & Engineering, 2020, vol. 8, p. 18148-18156.

Helan Xu et al., "Controlled De-Cross-Linking and Disentanglement of Feather Keratin for Fiber Preparation via a Novel Process", ACS Sustainable Chemistry & Engineering, 2014, vol. 2, p. 1404-1410.

Jin Zhu et al., "Reinforced Wool Keratin Fibers via Dithiol Chain Re-bonding", Advanced Functional Materials, 2023, No. 2213644, p. 1-10.

Jinlian Hu et al., "Wool Can Be Cool: Water-Actuating Woolen Knitwear for Both Hot and Cold", Advanced Functional Materials, 2020, vol. 30, No. 2005033, p. 1-9.

Xiaoyun Xu et al., "Reconstructed Hierarchically Structured Keratin Fibers with Shape-Memory Features Based on Reversible Secondary-Structure Transformation", Advanced Materials, 2023, vol. 35, No. 2304725, p. 1-9.

* cited by examiner

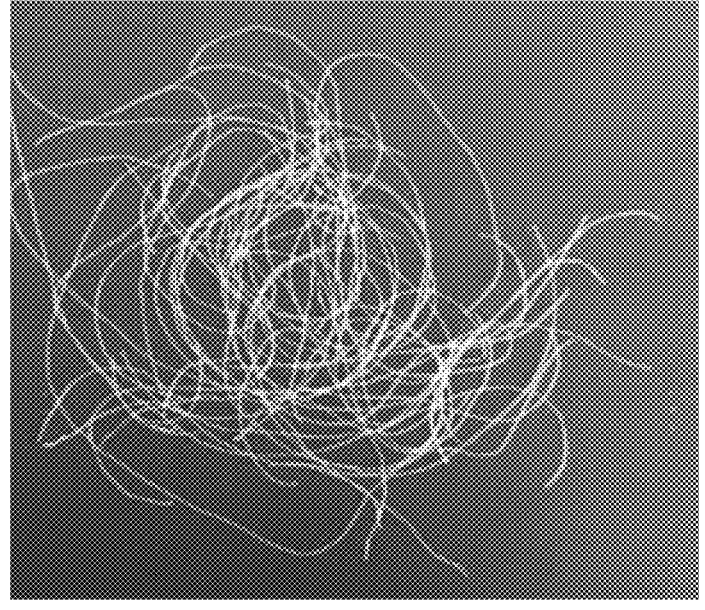
FIG. 3C
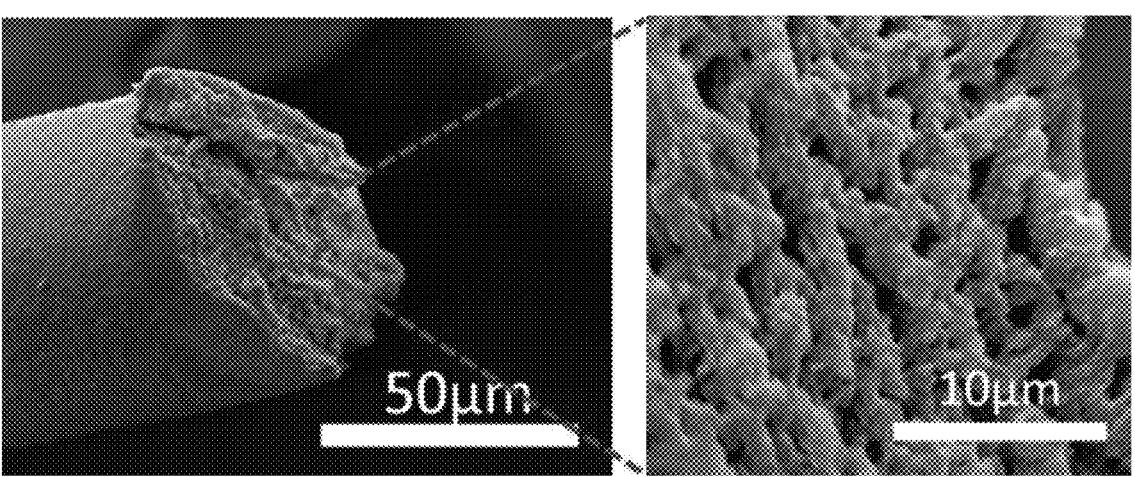
FIG. 3D
FIG. 3E

1

HYDRATION-RESPONSIVE SHAPE-MEMORY KERATIN COMPOSITE FIBERS AND FABRICATION METHODS THEREOF

CROSS-REFERENCE TO RELATED APPLICATIONS

The present application claims priority from U.S. provisional patent application Ser. No. 63/517,605 filed Aug. 3, 2023, and the disclosure of which is incorporated herein by reference in its entirety.

FIELD OF THE INVENTION

The present invention generally relates to the field of hydration-responsive smart fiber materials. More specifically the present invention relates to hydration-responsive shape-memory keratin composite fibers and fabrication methods thereof.

BACKGROUND OF THE INVENTION

Shape-memory materials have been extensively explored and applied in various fields, including aerospace, robotics, textiles and wearable devices, and biomedical engineering. The scope of exploration has broadened from alloys to polymer materials that offer enhanced flexibility, softness, biocompatibility, and biodegradability. Biological substrates such as cotton, wool, collagen, and spider silk have been studied as excellent shape-memory materials, focusing on their shape-memory mechanisms and application as actuators.

The shape-memory features in biological substrates originate from their structural metastability. The mechanism of the shape-memory effect in these substrates is associated with hydroresponsive functional groups and the reversible conformational variation of biomolecules. Consequently, biopolymers derived from these substrates exhibit remarkable potential as shape-memory device materials due to their superior biodegradability and biocompatibility. Despite extensive research on shape-memory materials, further investigation is required into reconstructing them with biomimetic long-range hierarchical structures from abundant biopolymer waste.

Researchers in the textile field have focused on manufacturing protein fibers that mimic natural protein fibers like wool, silk, and spider silk in both structure and functionality. Various methods, such as regeneration from biomass, chemical synthesis, and genetic engineering, are being explored to produce scalable products. However, despite these efforts, large-scale production has not yet been achieved. Wool waste, being one of the most abundant protein resources, is a valuable raw material for reconstructing biodegradable, biocompatible, and biomimetic keratin fibers as high-value-added biofibers. Currently, regenerated keratin fibers are fabricated using high keratin content and abundant surfactants, such as sodium dodecyl sulfonate (SDS), which are not environmentally friendly. While the fabrication protocol and mechanical properties of keratin fibers have been extensively studied, their potential applications as smart materials have not yet been fully explored.

Shape-memory fibers, a branch of stimuli-responsive materials, have found applications in many important fields, including aerospace, textiles and clothing, and biomaterial devices. With advancements in materials science, there is a growing trend to develop shape-memory materials that are biocompatible, biodegradable, and environmentally friendly. Biomacromolecular proteins are excellent candidates for shape-memory materials due to their hydrophilic groups and reversible macromolecular structures. Utilizing biological waste to prepare value-added fiber materials offers significant environmental and market value.

Currently, technologies have been developed to prepare regenerated keratin fibers from wool waste, duck feather waste, and other sources, demonstrating good mechanical properties. However, these technologies often involve complex and environmentally unfriendly formulations, and the wet stability of the fibers needs improvement. Additionally, no related technology has yet developed high-value hydration-responsive shape-memory regenerated keratin fibers.

Therefore, developing a hydration-responsive shape-memory regenerated keratin fiber from wool waste has significant environmental and market value, and the present invention addresses this need.

SUMMARY OF THE INVENTION

It is an objective of the present invention to provide material and/or method to solve the aforementioned technical problems. The present invention provides hydration-responsive shape-memory keratin composite fibers and their fabrication methods. These keratin composite fibers can be stretched in a wet state and dried to fix the shape, returning to their original length when exposed to hydration. The regenerated keratin fibers exhibit excellent water stability, water responsiveness, degradability, environmental friendliness, and cost-effectiveness.

In accordance with a first aspect of the present invention, a hydration-responsive shape-memory keratin composite fiber is provided. The hydration-responsive shape-memory keratin composite fiber includes a keratin network structure, having keratin $\alpha$-helices bonded by disulfide bonds; and cellulose nanocrystals (CNCs) for providing hydrogen bonds and stabilizing the structure of the keratin $\alpha$-helices to introduce a hydration-responsive switch. Particularly, the CNCs arrange and connect the keratin $\alpha$-helix to align the coil axis of the keratin $\alpha$-helices along the fiber axis.

In accordance with one embodiment of the present invention, when the keratin composite fiber encounters water, the hydrogen bonds are disrupted, causing the keratin $\alpha$-helix to uncoil and reform into $\beta$-sheet keratin subunits, making the keratin composite fiber stretchable to form a stretched keratin composite fiber.

In accordance with one embodiment of the present invention, the conformation of the stretched keratin composite fiber is fixed by drying, forming new hydrogen bonds to maintain the structure of the $\beta$-sheet keratin subunits.

In accordance with one embodiment of the present invention, the addition of CNCs promotes the formation of the $\beta$-sheet keratin subunits.

In accordance with one embodiment of the present invention, the fixed stretched keratin composite fiber is capable of being reformed to its original shape by re-humidifying the fixed stretched keratin composite fiber to break the new hydrogen bonds.

In accordance with one embodiment of the present invention, the CNCs serve as anchor points to retain the original shape.

In accordance with one embodiment of the present invention, the keratin composite fiber has a shape-fixity ratio of 90-95%.

In accordance with one embodiment of the present invention, the keratin composite fiber has a shape-recovery rate of at least 80%.

In accordance with one embodiment of the present invention, the keratin composite fiber exhibits a wet-extensibility of up to 360%.

In accordance with a second aspect of the present invention, a method of fabricating a hydration-responsive shape-memory keratin composite fiber is introduced. Specifically, the method includes the following steps:

conducting a reduction reaction on a keratin source for extracting keratin molecules utilizing L-cysteine and urea;

mixing the extracted keratin molecules, CNCs and a reducing agent in an alkaline solution to obtain a homogenous keratin spinning dope;

extruding the keratin spinning dope through a needle by a pump to a coagulation bath to form as-spun fibers;

oxidizing the as-spun fibers to generate disulfide bonds between $\alpha$-helices subunits; and crosslinking the keratin $\alpha$-helices to form hydration-responsive shape-memory keratin composite fibers.

In accordance with one embodiment of the present invention, the extruding is performed with an extrusion speed of 0.8-1 mL/h.

In accordance with one embodiment of the present invention, the keratin source includes wool, feathers, horns, hooves, mammalian hair, mammalian skin, mammalian nails and mammalian claws.

In accordance with one embodiment of the present invention, the coagulation bath is a sodium dihydrogen phosphate aqueous solution.

In accordance with one embodiment of the present invention, the coagulation bath has a pH less than 4.3 to facilitate keratin solidification and ion diffusion.

In accordance with one embodiment of the present invention, the crosslinking is utilizing glutaraldehyde as a cross-linker.

In accordance with a third aspect of the present invention, a humidity/hydration-sensitive textile actuator is provided. Particularly, the humidity/hydration-sensitive textile actuator incorporates the aforementioned hydration-responsive shape-memory keratin composite fibers.

In accordance with one embodiment of the present invention, the actuator is configured to generate torsional motion upon exposure to hydration.

In accordance with one embodiment of the present invention, the actuator is incorporated into a fabric to create a smart textile with dynamic, hydration-triggered motion capabilities.

In accordance with a fourth aspect of the present invention, a wound dressing including the aforementioned hydration-responsive shape-memory keratin composite fibers is provided.

In accordance with one embodiment of the present invention, the dressing contracts upon exposure to wound exudate to compress the wound.

BRIEF DESCRIPTION OF THE DRAWINGS

Embodiments of the invention are described in more details hereinafter with reference to the drawings, in which:

FIGS. 2A-2I depict the properties of the extracted keratin and spinning dope, in which FIG. 2A shows the extraction protocol of keratin from wool, FIG. 2B exhibits the CD spectra analysis of the extracted keratin and keratin spinning dope, FIG. 2C depicts the FTIR deconvolution analysis of amide I region of the extracted keratin solution, FIG. 2D demonstrates the amide I deconvolution analysis on the FTIR spectrum of the extracted keratin powder, FIG. 2E depicts the SDS-Page of extracted keratin, FIG. 2F shows that viscosity under an increasing shear rate of the keratin spinning dope, indicating a shear-thinning behavior, FIG. 2G shows the shear stress of the keratin spinning dope, FIG. 2H depicts the Raman spectroscopy analysis of keratin spinning dopes with and without CNCs, and FIG. 2I depicts the FTIR deconvolution analysis of the amide I region of keratin at varying CNCs concentrations, demonstrating CNCs' effect of increasing $\beta$-sheet content;

FIGS. 3A-3H depict the fiber formation and structural analysis of fabricated keratin fibers, in which FIG. 3A illustrates the wet-spinning process, including coagulation, oxidation, and cross-linking, FIG. 3B depicts the FTIR spectrum of fibers at the three stages of wet-spinning, FIG. 3C is a digital photograph of the homogenous regenerated keratin fibers, FIG. 3D is a SEM image of a single keratin fiber, showing a smooth surface, FIG. 3E is a zoom-in of the cross section of the fiber, indicating a hierarchical structure, FIG. 3F depicts a polarized optical microscopy image showing the anisotropic birefringence of a single keratin fiber, FIG. 3G exhibits a SAXS scattering profile of keratin fibers from different detecting directions, and FIG. 3H is an illustrative schematic of the keratin fiber structure composed of $\alpha$-helices coils and CNCs that are aligned along the fiber axis;

FIGS. 4A-4N depict the hydration-responsive shape-memory effect of fabricated keratin fibers, in which FIG. 4A depicts an illustrative schematic of keratin protein secondary-structure transformation from the $\alpha$-helix to $\beta$-sheets under axial strain, FIG. 4B demonstrates an illustration of five specific shape-memory programming stages, FIG. 4N is a net-point model to elaborate the mechanism of the shape-memory effect;

FIGS. 5A-5C depict the application of keratin composite fibers, in which FIG. 5A is an illustrative schematic of the fabrication process of keratin fiber into an artificial muscle with a ply yarn structure, FIG. 5B shows the self-twisting effect of the keratin torsional muscle triggered by water and drive the glass paddle to rotate, and FIG. 5C depicts an application scenario as smart bandage of hydration-responsive fabrics with regenerated keratin torsional muscle;

DETAILED DESCRIPTION

Figure 1:
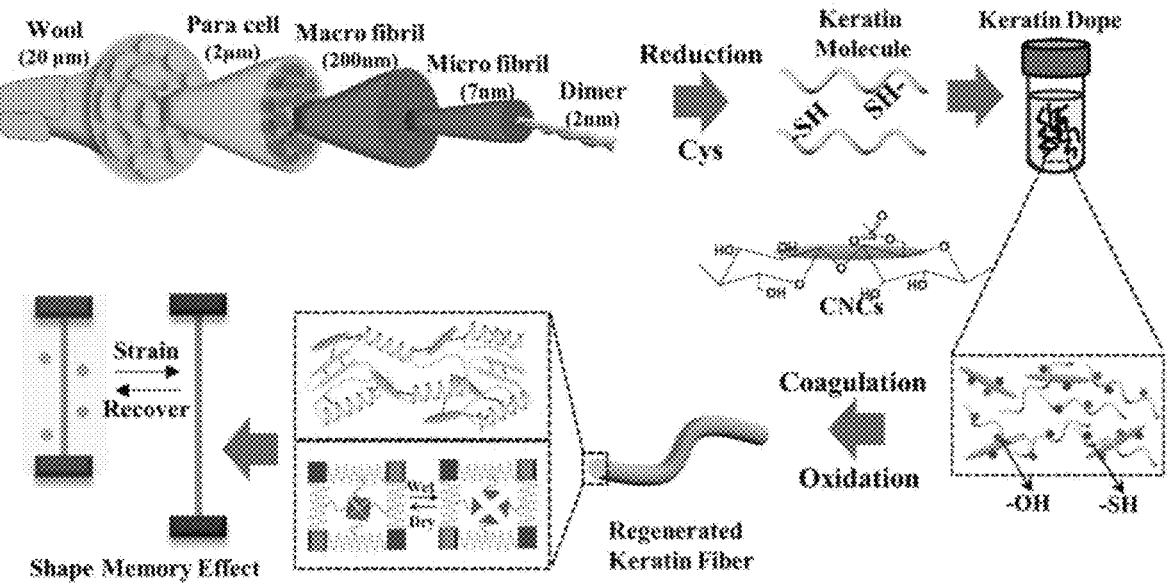
FIG. 1 depicts an overview of the design and fabrication of hydration-responsive shape-memory keratin composite fibers, showing the schematic of the hierarchical structure of wool fibers, mechanism for keratin extraction, molecular structure within the spinning dope, secondary structure of the regenerated keratin fibers, model illustration of the mechanism of the shape-memory effect, and shape-memory effect performance.

In the following description, materials and/or preparation methods of hydration-responsive regenerated keratin fiber and the likes are set forth as preferred examples. It will be apparent to those skilled in the art that modifications, including additions and/or substitutions may be made without departing from the scope and spirit of the invention. Specific details may be omitted so as not to obscure the invention; however, the disclosure is written to enable one skilled in the art to practice the teachings herein without undue experimentation.

Keratin is a family of fibrous structural proteins that are key components in the outer layer of human skin, as well as in hair, nails, feathers, hooves, and horns. These proteins are known for their mechanical strength and protective qualities, making them essential for maintaining the integrity of cells that are exposed to the external environment. Among the types of keratin, $\alpha$-keratin (alpha-keratin) is particularly notable. $\alpha$-Keratin is a type of keratin found predominantly in mammalian hair, skin, and nails. It is characterized by its helical structure, which is stabilized by disulfide bonds. This helical structure contributes to the protein's elasticity and strength.

Keratin proteins typically exist as dimers, which means they are composed of two subunits. These subunits are usually coiled around each other to form a helical structure, known as the $\alpha$-helix. Each keratin molecule can be divided into two major types of subunits: type I (acidic) and type II (basic to neutral). The formation of a dimer involves one type I and one type II keratin subunit. The interaction between these subunits, through various types of bonding (including disulfide bonds), contributes to the stability and mechanical properties of the keratin filament.

The $\alpha$-helix is a common structural motif in proteins, characterized by a right-handed coil where each amino acid residue corresponds to a 100-degree turn in the helix. In $\alpha$-keratin, the $\alpha$-helical structure is a critical feature that enables the formation of coiled-coil dimers. These dimers further assemble into larger structures, such as protofilaments and microfibrils, which are the building blocks of the fibrous keratin networks in cells.

Keratin is a versatile and robust protein that plays a crucial role in the structural integrity of various biological tissues. $\alpha$-Keratin, a specific form of keratin, is distinguished by its helical structure and the formation of dimers composed of type I and type II subunits. These dimers assemble into larger filaments, providing the mechanical strength and resilience necessary for protecting and supporting cells in hair, skin, and nails. The $\alpha$-helix structure within $\alpha$-keratin is central to its function, enabling the formation of strong, elastic, and durable fibers.

The shape-memory effect observed in various animal hairs results from the reversible change of $\alpha$-helices and $\beta$-sheets in the protein conformation when a load is applied or released along the longitudinal axis. Wool fibers include 90% proteins, with keratin constituting 80-85% of the protein content. The principal conformation of keratin is $\alpha$-helical in nature. Taking advantage of this characteristic, the present invention aims to design and produce bioinspired shape-memory keratin fibers by preserving the principal conformation of the original keratin raw materials In accordance of a first aspect of the present invention, a hydration-responsive shape-memory keratin composite fiber is provided. These keratin composite fibers consist of a keratin network structure, which includes keratin $\alpha$-helices bonded by disulfide bonds. Additionally, cellulose nanocrystals (CNCs) are incorporated to provide hydrogen bonds and stabilize the structure of the keratin $\alpha$-helices, thereby introducing a hydration-responsive switch. The CNCs are strategically arranged to connect the keratin $\alpha$-helices, aligning the coil axis of the keratin $\alpha$-helices along the fiber axis.

When the keratin composite fiber encounters water, the hydrogen bonds within the fiber are disrupted. This disruption causes the keratin $\alpha$-helices to uncoil and reform into $\beta$-sheet keratin subunits. This transformation makes the keratin composite fiber stretchable, allowing it to form a stretched keratin composite fiber. The conformation of the stretched keratin composite fiber can be fixed by drying, during which new hydrogen bonds are formed to maintain the structure of the $\beta$-sheet keratin subunits. The addition of CNCs benefits the formation of these $\beta$-sheet keratin subunits, enhancing the overall structure and functionality of the fiber.

Furthermore, the fixed stretched keratin composite fiber is capable of being reformed to its original shape. This reformation occurs by re-humidifying the fixed stretched keratin composite fiber, which breaks the new hydrogen bonds that are formed during the drying process. The CNCs serve as anchor points during this process, helping to retain the original shape of the fiber.

The keratin composite fiber described herein exhibits a shape-fixity ratio of 90-95%, indicating its ability to maintain a temporary shape until it is reactivated by water. Additionally, the keratin composite fiber has a shape-recovery rate of at least 80%, demonstrating its efficiency in returning to its original form. Furthermore, the keratin composite fiber exhibits a wet-extensibility of up to 360%, showcasing its remarkable flexibility and durability in wet conditions.

Overall, the regenerated keratin fibers are more efficient, environmentally friendly, and cost-effective through the addition of CNCs. The reversible transition of keratin secondary structure from $\alpha$-helix to $\beta$-sheet is hypothesized as the primary mechanism for the water-triggered shape-memory keratin fibers, as the hierarchical structure containing $\alpha$-helix and $\beta$-sheet has been successfully restored within the keratin fibers. In this system, hydrogen bonds act as the switches that "open" and "close" upon water treatment (FIG. 1). After being freed from hydrogen bridging, the $\alpha$-helices, which act as springs, become deformable under strain. In this deformation and restoration process, the disulfide bonds and CNCs act as net points that preserve the permanent shape. Owing to the preservation of the secondary structure of the keratin protein during extraction, the regenerated keratin fibers exhibit a significant shape-memory effect similar to that of natural protein fibers. Keratin fibrils connected by CNCs self-arrange into a nematic phase under shear stress, allowing fibril axial alignment during extrusion. In addition to the investigation of the continuous fabrication and properties of shape-memory fibers, processability has made it possible to construct fabrics/textiles that change the macroscopic architecture upon water stimulation. This inherently biodegradable and biocompatible shape-memory system exhibits great potential for use as a textile actuator in robotics and smart biomedical devices.

In accordance of a second aspect of the present invention, a method for fabricating hydration-responsive shape-memory keratin composite fibers is introduced. The process begins by conducting a reduction reaction on a keratin source to extract keratin molecules. This reduction reaction utilizes L-cysteine and urea as agents to break down the keratin structure from its source. The keratin source can include materials such as wool, feathers, horns, hooves, mammalian hair, mammalian skin, mammalian nails, and mammalian claws, all of which are rich in keratin.

Once the keratin molecules are extracted, they are mixed with CNCs and a reducing agent in an alkaline solution. This mixture results in a homogeneous keratin spinning dope, which is essential for the subsequent fiber formation process. The keratin spinning dope is then extruded through a needle using a pump, at an extrusion speed of 0.8-1 mL/h, into a coagulation bath. The coagulation bath, which is a sodium dihydrogen phosphate aqueous solution with a pH less than 4.3, facilitates the solidification of keratin and promotes ion diffusion, leading to the formation of as-spun fibers.

The as-spun fibers are then subjected to an oxidation process to generate disulfide bonds between the $\alpha$-helix subunits of the keratin molecules. This step is crucial as it leads to the formation of keratin $\alpha$-helices, which are integral to the structure of the final composite fibers. Following the oxidation, the keratin $\alpha$-helices are crosslinked to enhance the stability and functionality of the fibers. Glutaraldehyde is used as a crosslinker in this step, ensuring the robustness and integrity of the hydration-responsive shape-memory keratin composite fibers.

This method effectively produces keratin composite fibers that possess hydration-responsive shape-memory properties, making them highly suitable for various applications. The described process is not only efficient but also environmentally friendly, leveraging natural keratin sources and minimizing the use of harmful chemicals. By incorporating CNCs and employing precise fabrication techniques, the resultant keratin composite fibers exhibit excellent mechanical properties and responsiveness to water, positioning them as advanced materials in the field of smart textiles and biomedical devices.

In one embodiment, for keratin extraction, a certain proportion of washed wool, urea, and reducing agent are mixed in deionized water, and heated at 80-90° C. for 12-24 h. Insoluble impurities are removed by filtration, and excess urea and reducing agent are removed by dialysis. It is dried and ground to obtain keratin powder for use.

For preparing a keratin spinning dope, a certain proportion of keratin powder, cellulose nanocrystals, and reducing agent are dissolved in deionized water, and adjust the pH value to alkaline (around pH 11-12). Stir until the solid powder dissolves to obtain the spinning dope A, which is left to stand for later use.

Wet spinning is used to prepare regenerated keratin fibers. The above-prepared spinning dope A is extruded through 27-21 G needles by a pump, with an extrusion speed of 0.8-1 mL/h, into the coagulation bath to form fibers. The obtained as-spun fibers are stabilized in a coagulation bath for 0.5-1 h. The above-mentioned as-spun keratin fibers are transferred to an oxidation bath for 0.5-1 h, and then transferred to a crosslinking bath for 1-5 min for crosslinking treatment. Finally, the surface impurities and unreacted materials are washed away with deionized water.

In some embodiments, the solid-to-liquid ratio in keratin extraction is: 1:17, and the urea concentration is 8 M. The reducing agent is L-cysteine and the ratio of it to wool is 1:10.

The cellulose nanocrystals are hydrolyzed products of sulfuric acid with a diameter of 5-20 nm and a length of 100-200 nm. Particularly, the mass range of keratin, cellulose nanocrystals, and reducing agent (cysteine) is 15:0.5: 1.5 to 20:2:2.

In some embodiments, the coagulation bath is a 0.8 M sodium dihydrogen phosphate aqueous solution; the oxidation bath is sodium dihydrogen phosphate and hydrogen peroxide aqueous solution, and the ratio of the two to water is 9.6:1:100. Further, the cross-linking bath is an aqueous glutaraldehyde solution with a concentration range of 2.5%-5.0%.

In accordance of a third aspect of the present invention, a humidity and hydration-responsive textile actuator is demonstrated. The actuator leverages the above-mentioned keratin composite fiber, including its hydration-responsiveness and shape-memory effects.

Specifically, the humidity-sensitive textile actuator is designed to harness the fiber's ability to respond to moisture. When incorporated into textiles, these actuators can generate torsional motion upon exposure to water. This torsional motion is facilitated by the unique structure of the keratin composite fiber, where the keratin $\alpha$-helices and CNCs interact to produce a responsive behavior to hydration changes. The CNCs provide critical hydrogen bonding and structural stabilization, enabling the fiber to uncoil and realign its molecular structure when wetted.

Furthermore, these actuators can be seamlessly integrated into fabrics to create smart textiles with dynamic, water-triggered motion capabilities. Such smart textiles can react to environmental humidity or direct water exposure, resulting in movements that can be harnessed for various practical applications, from wearable technology to innovative responsive clothing designs. This integration not only enhances the functional value of textiles but also opens new avenues in the development of advanced materials with built-in responsiveness to environmental stimuli.

In accordance of a fourth aspect of the present invention, a wound dressing adopting the above-mentioned keratin composite fiber is exhibited.

The wound dressing incorporates the hydration-responsive shape-memory keratin composite fiber, which exhibits remarkable capabilities in response to moisture changes. Upon exposure to wound exudate or moisture, the dressing undergoes a contraction phase, facilitating a snug fit around the wound area. This contraction is facilitated by the intrinsic shape-memory properties of the keratin composite fiber, where the keratin $\alpha$-helices and CNCs collaborate to enable structural realignment and dimensional change in response to hydration.

Moreover, this capability to contract around the wound site not only ensures a better fit but also optimizes compression therapy. By maintaining constant, gentle pressure on the wound area, the dressing promotes effective wound closure and accelerates the healing process. This compression therapy is crucial in managing wounds, particularly chronic wounds or those with irregular shapes, where maintaining proper pressure and moisture levels is essential for healing.

The incorporation of the hydration-responsive shape-memory keratin composite fiber into wound dressings represents a significant improvement over traditional material. It offers enhanced biocompatibility, biodegradability, and environmental friendliness compared to synthetic polymers, while also providing superior functionality through its dynamic response to moisture.

EXAMPLES

Figures 2A, 2B:
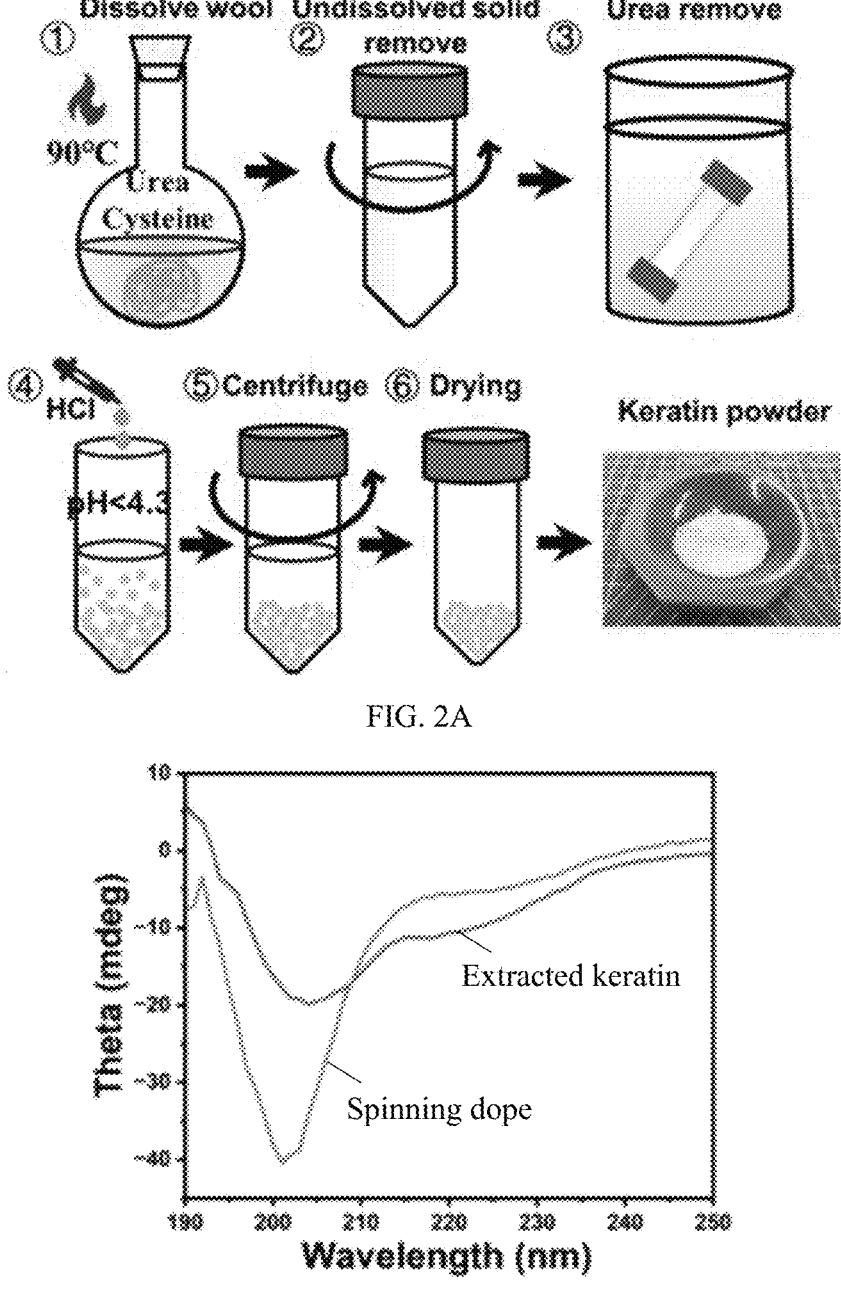

Example 1. Keratin Extraction and Rheological Properties of the Spinning Dope Keratin molecules in animal hair are compactly stacked, with the smallest units being dimers connected by strong disulfide bonds. As illustrated in FIG. 1, fibrillar keratin is extracted from wool using urea, which acts as a swelling agent to loosen the cortical cells through the degradation of hydrogen bonds. Additionally, the strong disulfide bonds in the dimers are broken to release fibrous keratin molecules from the hair structure. L-cysteine is used along with urea in the extraction process to cleave the disulfide bonds, yielding two hydro-sulfonyl groups. This reaction is reversible under reductive and oxidative conditions, allowing for the reconstruction of disulfide linkages during subsequent material fabrication. Keratin is extracted from an aqueous solution containing urea and L-cysteine at high temperatures (FIG. 2A). The wool residue is then removed via centrifugation. After removing excess urea through dialysis, keratin protein is isolated from the suspension through phase separation under acidic conditions. This method is reversible, ensuring the restoration of keratin conformation during the material fabrication process.

Figure 2C:
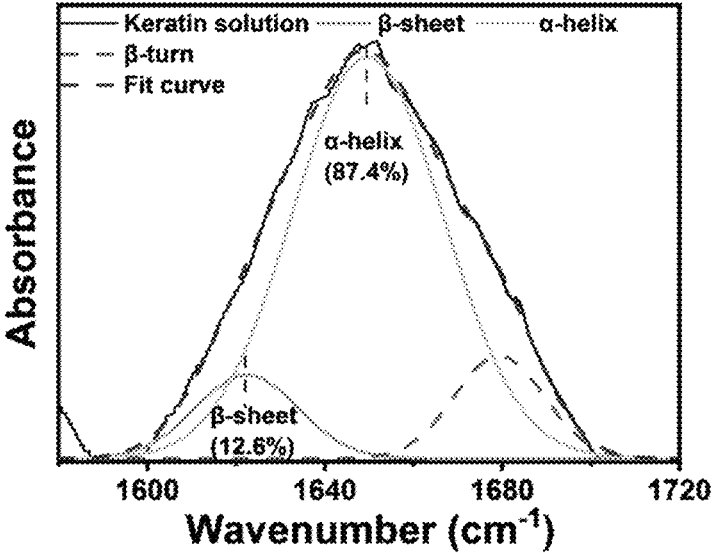
Figure 2D:
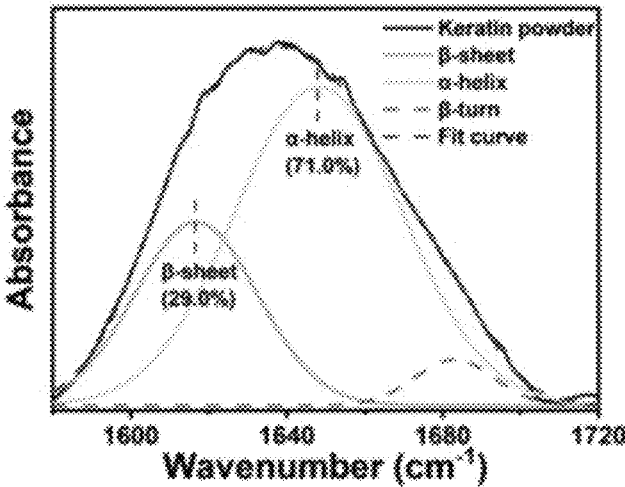
Figure 2E:
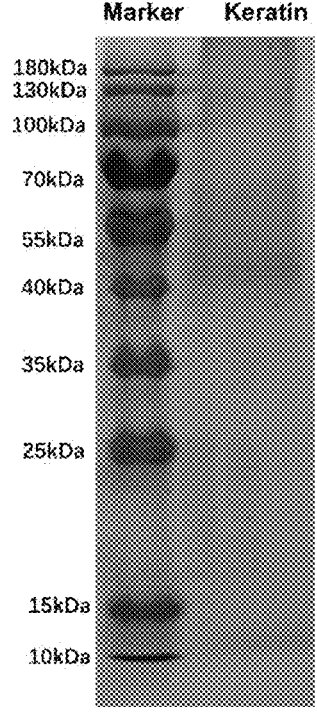

After the non-destructive extraction process, the preservation of α-helices and coil architecture is confirmed using a circular dichroism (CD) spectrum (FIG. 2B) and the deconvolution analysis of the amide I region (1600-1700 cm$^{-1}$) on the Fourier transform infrared (FTIR) spectrum (FIG. 2C), which exhibits a high content of α-helix conformation. The α-helix content is also preserved in the powder format (FIG. 2D), indicating the reversible change of the secondary structure. This is further confirmed through SDS-polyacrylamide gel electrophoresis (SDS-PAGE) analysis, which exhibits a specific band at 10-11 kDa, representing a dimer of the coiling architecture with minimal protein degradation (FIG. 2E). Because keratin is sedimented under an isoelectric point, it is re-dissolvable under alkaline conditions, resulting in a non-destructive structure. Preservation of the molecular backbone and destruction of the cross-linked structure results in the favorable spinnability of the extracted keratin.

Figure 2F:
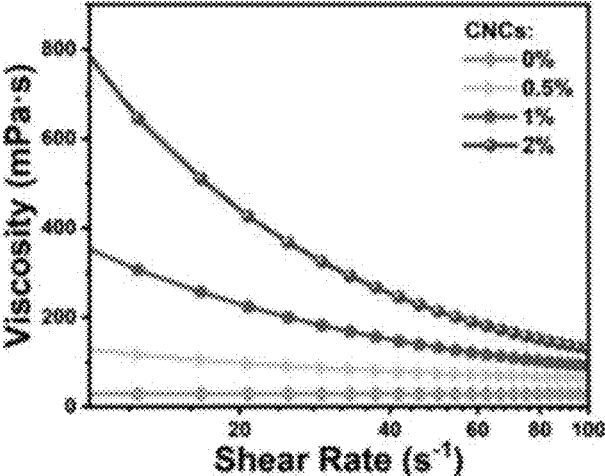
Figure 2G:
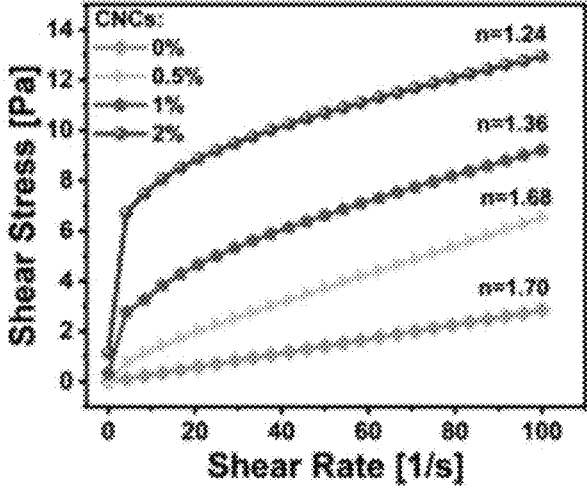
Figure 2H:
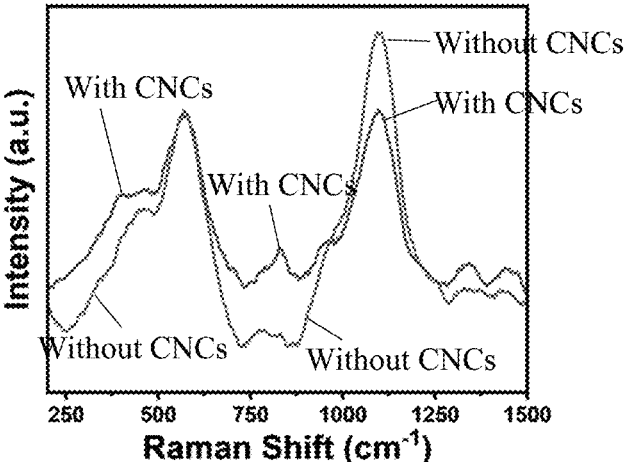
Figure 2I:
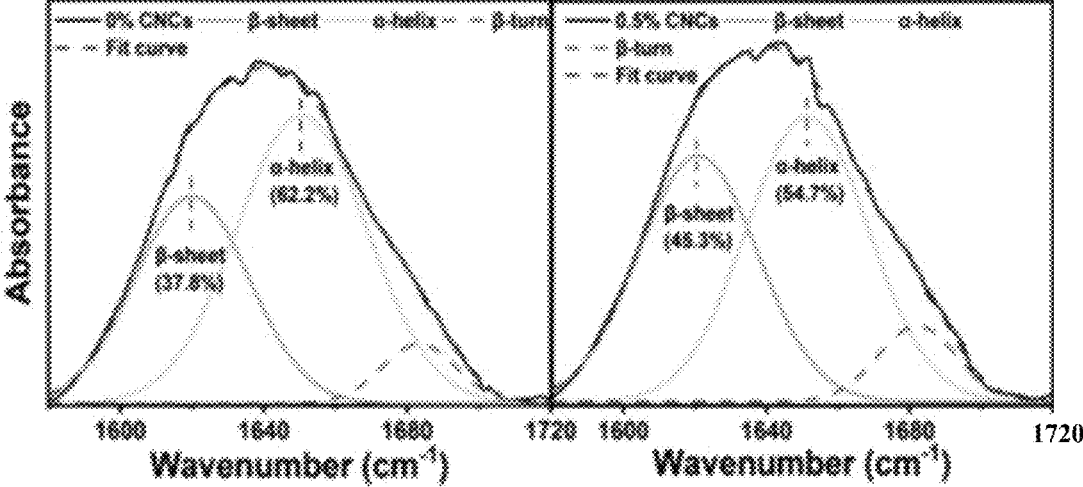
Figure 2I:
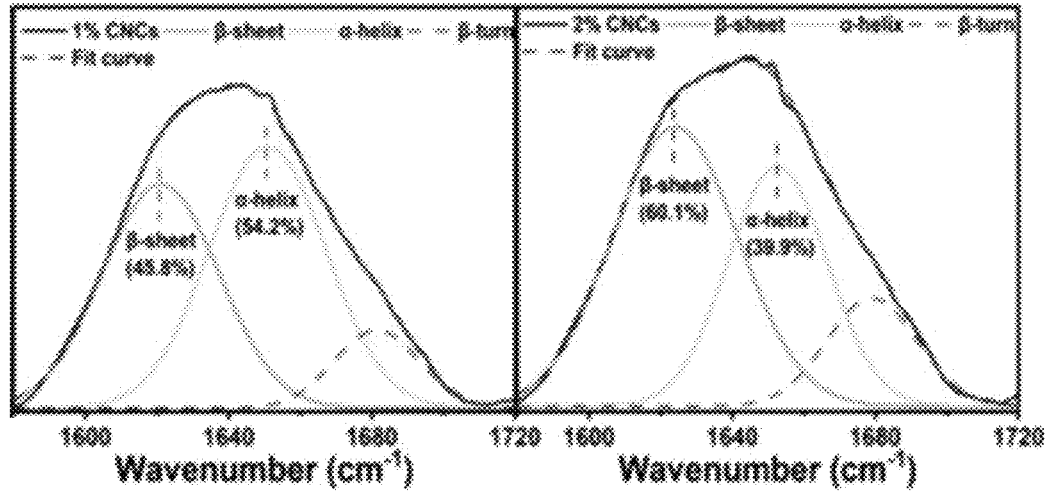

The alkaline keratin solution appears greenish and non-viscous. The rheological properties of the solution exhibit lower viscosity, resembling the behavior of a Newtonian liquid. Generating continuous fibers after ejection into the coagulation bath is relatively difficult. Therefore, a small amount of CNCs (obtained from cellulose through sulfuric acid hydrolysis) is added to the spinning dopes to improve spinnability because CNCs have been reported to enable the unfolding of protein molecules via hydrogen bonds. The keratin-spinning dope becomes viscous with the addition of CNCs. The addition of a small amount of CNCs has a significant impact on the rheological properties of the keratin-spinning dope. This can be attributed to the unfolding and interconnection effects of CNCs. The viscosity at low shear rates increases significantly in the presence of CNCs (FIG. 2F). Shear thinning is observed, which is considered synonymous with pseudo-plastic behavior. Through a more comprehensive and systematic analysis of the flow behavior and rheological properties, it is determined that the keratin spinning dope with a higher content of CNCs exhibits a lower value of the non-Newtonian exponent (n), signifying higher long-chain cross-linking with enhanced spinnability (FIG. 2G). This enhancement results from the partially linear connection of CNCs between keratin molecules through disulfide and hydrogen bonds. The disulfide bond connection is supported by the Raman spectrum analysis of the disulfide content, as determined from the peak region at 560 cm$^{-1}$ (FIG. 2H). The interaction between CNCs and keratin may alter the secondary structure of keratin. The deconvolution of the FTIR spectra in the amide I region further supports that CNCs partially change the keratin protein conformation from α-helix to β-sheet (FIG. 2I). Table 1 lists the secondary structures of keratins with varying percentages of CNCs.

TABLE 1

Secondary structure content of keratin under different conditions

| Samples | | α-helix and random coil (1650 cm$^{-1}$) | β-sheet (1620 cm$^{-1}$) | β-turn (1680 cm$^{-1}$) |
|---|---|---|---|---|
| Extracted keratin solution | | 77.3 | 10.9 | 11.8 |
| Keratin powder | | 67.2 | 28.2 | 4.60 |
| Keratin with CNCs | 0% | 57.4 | 35.8 | 6.80 |
| | 0.5% | 49.9 | 41.6 | 8.50 |
| | 1% | 48.5 | 41.0 | 10.5 |
| | 2% | 34.7 | 51.0 | 14.3 |
| Wet keratin fiber with 2% CNCs | | 67.2 | 32.8 | — |

Example 2. Fiber Formation and Hierarchical Structural Analysis

The alignment of polymer molecules along the axial direction is crucial for achieving a compact fiber structure and enhancing mechanical properties. When biomacromolecules, such as α-helices, are aligned along the pulling direction, maximum uncoiling of these biomacromolecules and increased intermolecular friction can be obtained, resulting in a greater tensile failure strain. As previously mentioned, CNCs connect keratin molecules and facilitate their organization into a nematic phase in the shear direction under shear stress, thereby enabling the formation of an anisotropic structure.

Figure 3A:
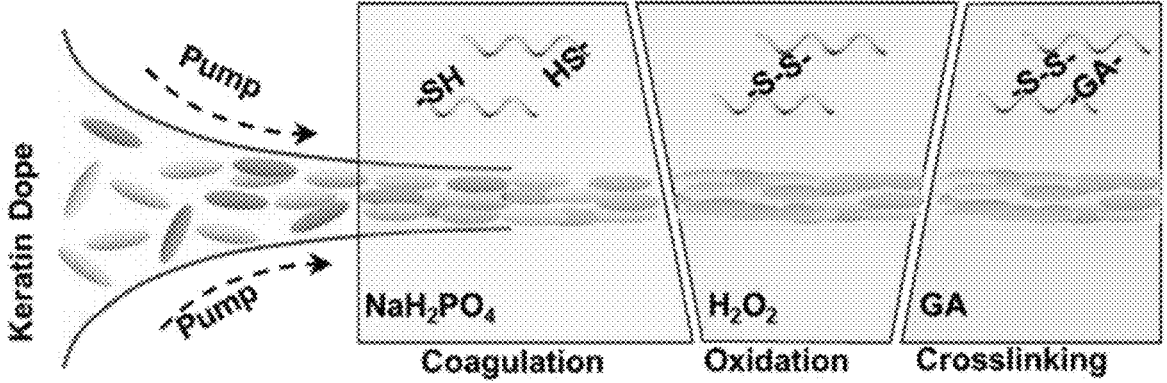
Figure 3B:
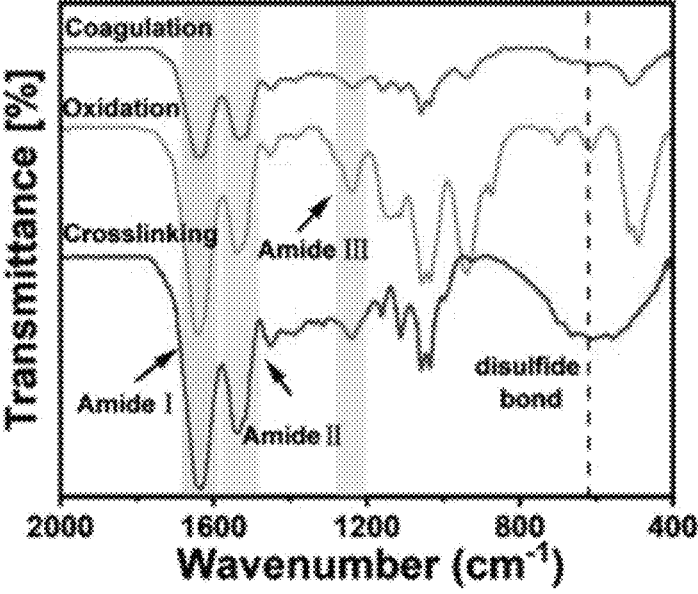
Figure 6A:
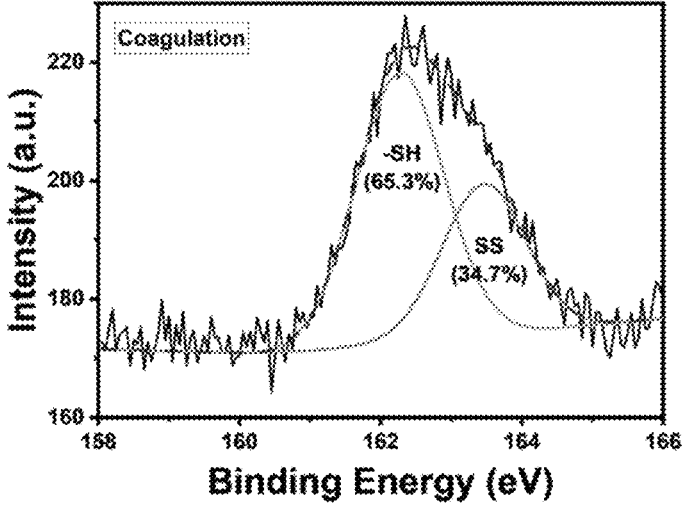
FIGS. 6A-6C depict the sulfur XPS spectra of keratin fibers in the three spinning steps, showing that the content of disulfide bonds is increased after the oxidation while thiol groups decreased, in which FIG. 6A directs to the coagulation step, FIG. 6B relates to the oxidation step, and FIG. 6C associates with the crosslinking step.
Figure 6B:
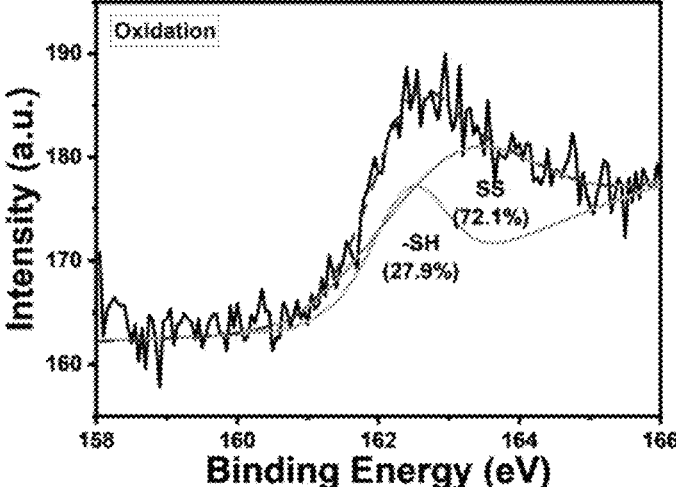
Figure 6C:
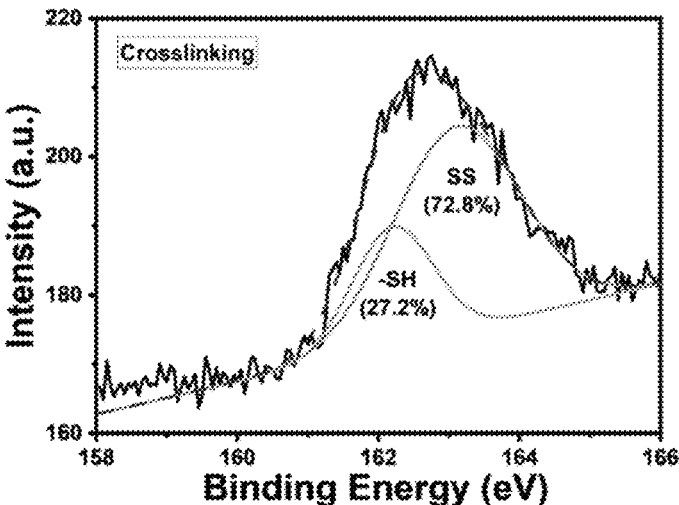

Therefore, the conventional fiber manufacturing approach of wet spinning is adopted to produce keratin fibers, as illustrated in FIG. 3A. The acidic solution, pH<4.3, contained 0.8 m sodium dihydrogen phosphate (NaH$_2$PO$_4$) is used as the coagulation bath, which enables keratin solidification and ion diffusion. The re-bridging of disulfide bonds on the cysteine thiol groups occurs under oxidation conditions that involves the presence of hydrogen peroxide ($H_2O_2$), thereby strengthening the α-helix structure. This result is supported by a clear absorption band observed at 610 cm$^{-1}$, representing the disulfide bonds on the FTIR spectrum (FIG. 3B). Sulfur X-ray photoelectron spectroscopy (XPS) results shown in FIGS. 6A-6C further confirm the re-bridging of disulfide bonds. Especially in FIG. 6B, the content of disulfide bonds increases after the oxidation while thiol groups decrease. The compact structure within the keratin fibers is further enhanced by glutaraldehyde cross-linking of the hydrophilic functional groups to improve water stability and mechanical properties. Characteristic absorption bands assigned to peptide bonds (—CONH—) are detected using the FTIR spectrum (FIG. 3B). The absorption band 1700-1600 cm$^{-1}$ corresponds to amide I, 1540-1520 cm$^{-1}$ corresponds to amide II, and 1300-1220 cm$^{-1}$ corresponds to amide III, indicating the presence of secondary structures in the keratin protein.

Figure 3F:
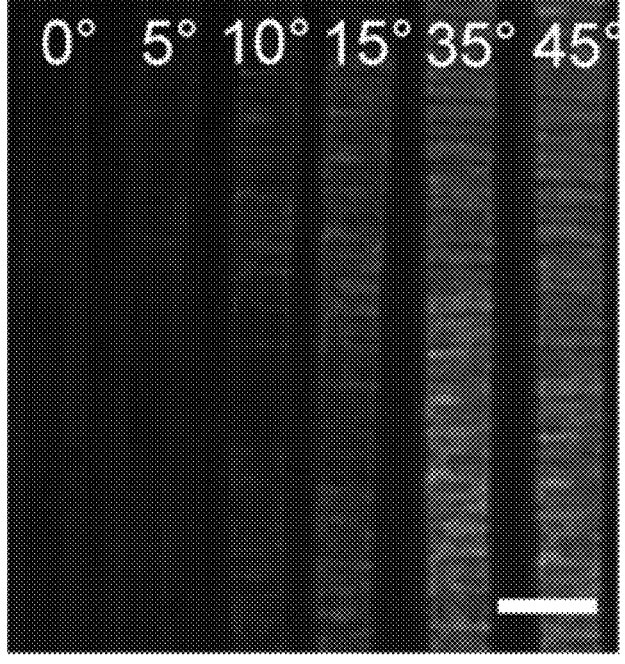
Figure 3G:
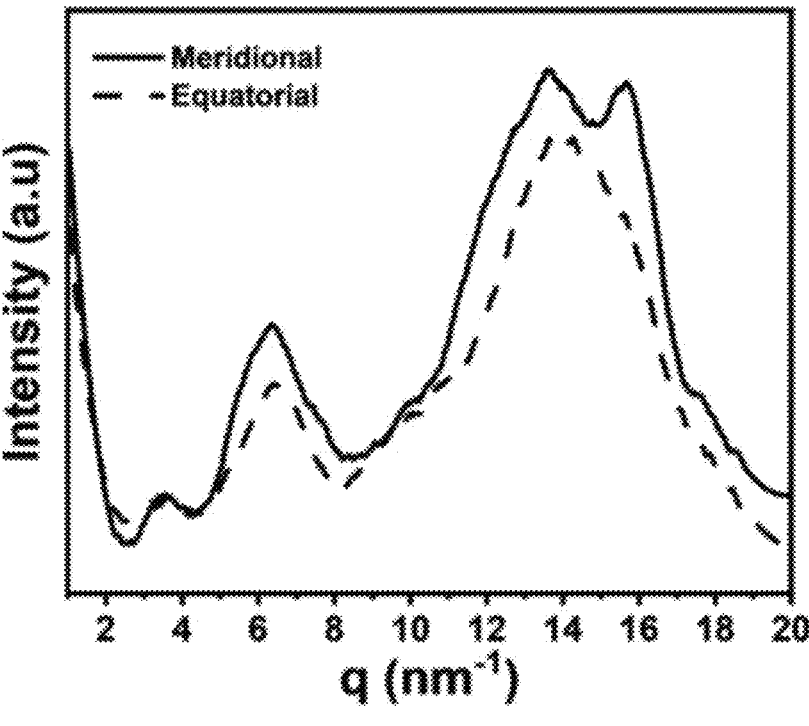
Figure 3H:
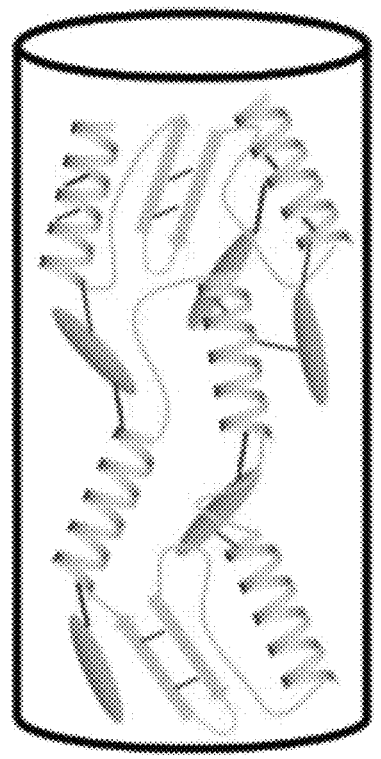
Figure 7:
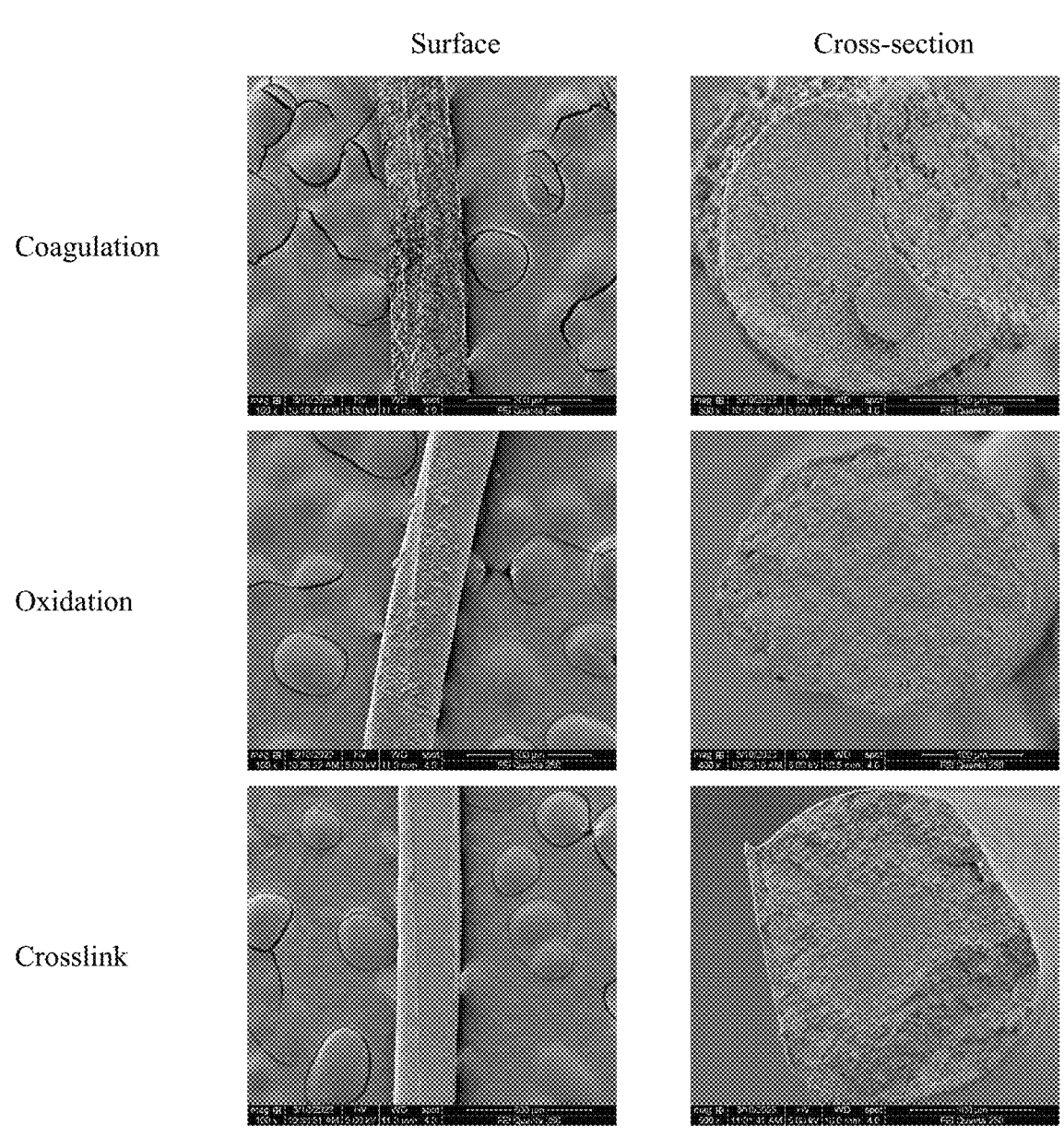
FIG. 7 depicts the scanning electron microscope (SEM) images of keratin fiber spun via 27 G needle.

This well-designed fabrication procedure allows for the production of continuous and homogeneous fibers (FIG. 3C). To further analyze the hierarchical microstructure of the regenerated keratin fibers, scanning electron microscopy (SEM) observations are conducted (FIG. 3D). As shown in FIG. 7, the scanning electron microscope images displaying the surface and cross-section morphologies of keratin fibers under different spinning stages suggest that the microstructure evolves during the three fiber-forming steps and ultimately results in homogeneous fibers with a smooth surface. The magnified SEM image of the cross-section indicates that the fiber is composed of stacked solid sheets (FIG. 3E). Polarized optical microscopy (POM) further confirms the anisotropic structure by demonstrating the birefringence behavior and maximum light intensity at 45° under cross-polarizers (FIG. 3F). Additional insight into the hierarchical structure and anisotropy is achieved using small-angle X-ray scattering (SAXS). The meridional and equatorial directions yield varying spectra (FIG. 3G). As illustrated in FIG. 3H, keratin molecules in α-helix and β-sheet conformations are arranged along the fiber axis and connected by CNCs.

Example 3. Hydration-Responsive Shape-Memory Features of Keratin Fibers

Figure 8A:
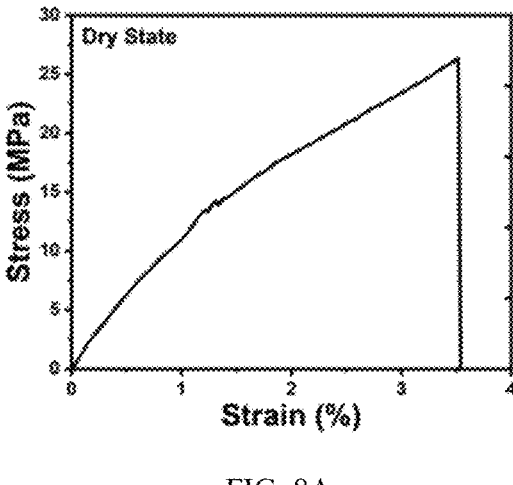
FIGS. 8A-8B depict the representative strain-stress curves of keratin fibers at dry (FIG. 8A) and wet (FIG. 8B) state.
Figure 8B:
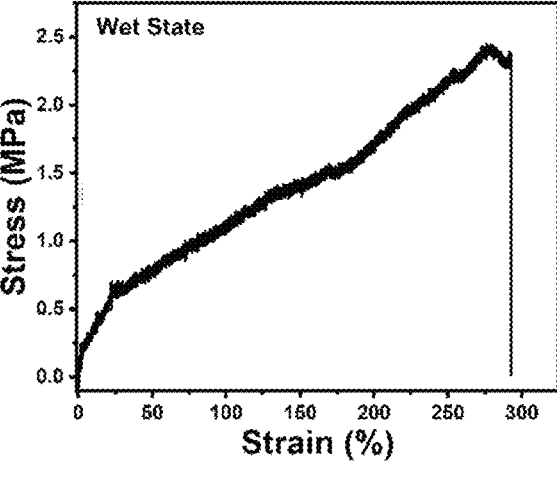

With the addition of CNCs, the keratin network structure is stabilized and enhanced through physical reinforcement, hydrogen bond connections, and disulfide bond bridging. This results in an improvement in the mechanical properties, significantly enhancing the hydration-responsive effect. The tensile stress of the regenerated keratin fibers reaches 22.6±2.67 MPa in the dry state. After wetting, the maximum tensile stress reduces to 2.71±0.280 MPa but exhibits a maximum strain of 362±15.9% (FIG. 8A and FIG. 8B), demonstrating outstanding stretchability. The invasion of water molecules disrupts the hydrogen bonds, freeing the long-range ordered protein molecules, which is influential in the shape-memory programming process that requires force loading along the fiber axis.

Figure 4A:
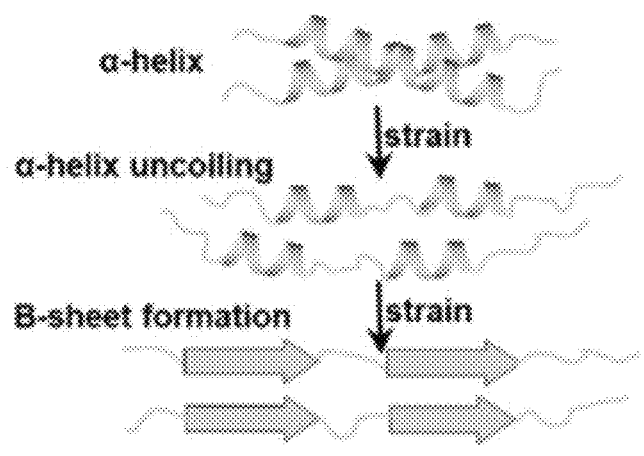
Figure 4B:
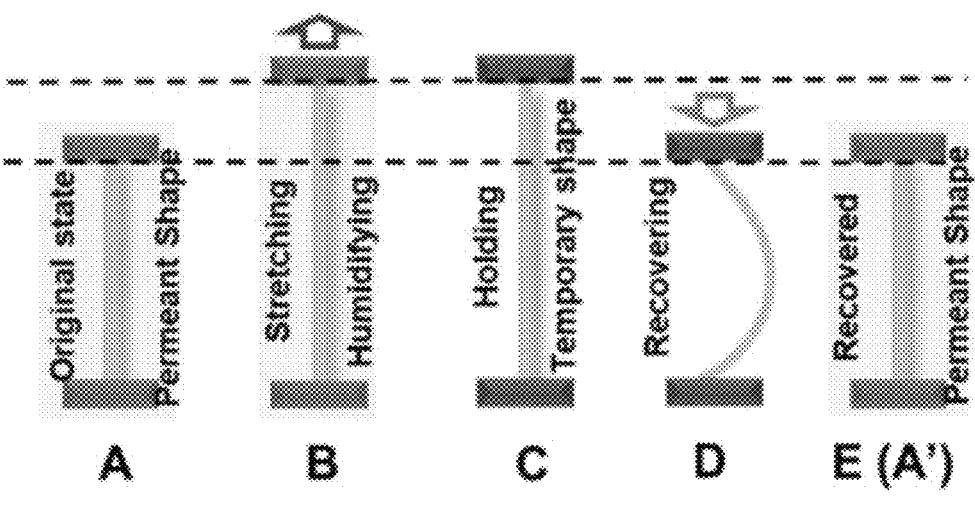
Figure 4C:
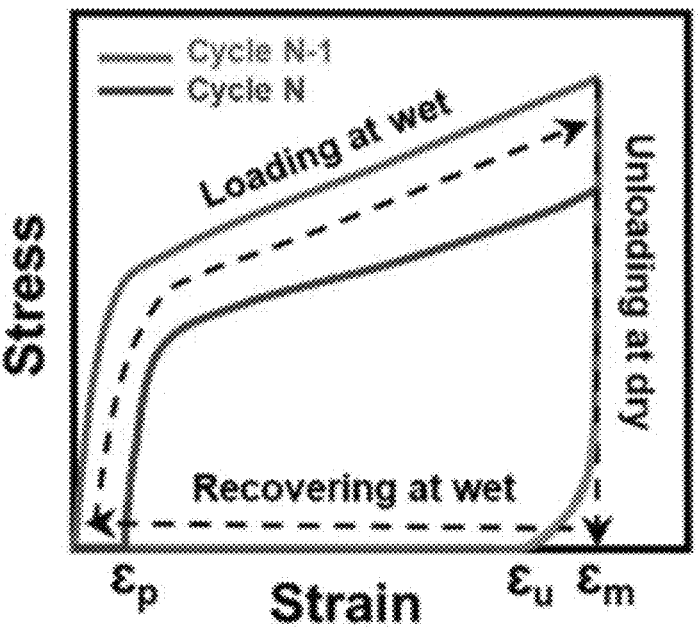
FIG. 4C shows the representative shape-memory programming cycle curves of shape-memory fixity ratio and shape-recovery rate calculations.

The shape-memory effect in keratin fibers depends on the reversible uncoiling of the α-helices and the formation of β-sheets under uniaxial strain and water stimulation (FIG. 4A). A shape-memory programming procedure is carried out to confirm this mechanism, as shown in FIG. 4B, with five specific stages. The specific strain-stress curves of shape-memory materials are illustrated in FIG. 4C and can be divided into three important stages: stretching under wet conditions, unloading under dry conditions, and recovering under wet conditions. Further investigation of the shape-memory cycles allows for the determination of two key indices (shape-fixity ratio, $R_f$, and shape-recovery rate, $R_r$) to quantify the shape-memory properties. These indices are calculated using the following equations:

$$R_f = \frac{\varepsilon_u\ (N)}{\varepsilon_m} \times 100 \tag{1}$$

$$R_r = \frac{\varepsilon_m - \varepsilon_p(N)}{\varepsilon_m} \times 100 \tag{2}$$

where $\varepsilon_m$ represents the maximum strain, $\varepsilon_u$ is the fixed strain after unloading the fibers, and $\varepsilon_p$ is the residual strain after recovery.

Figure 4D:
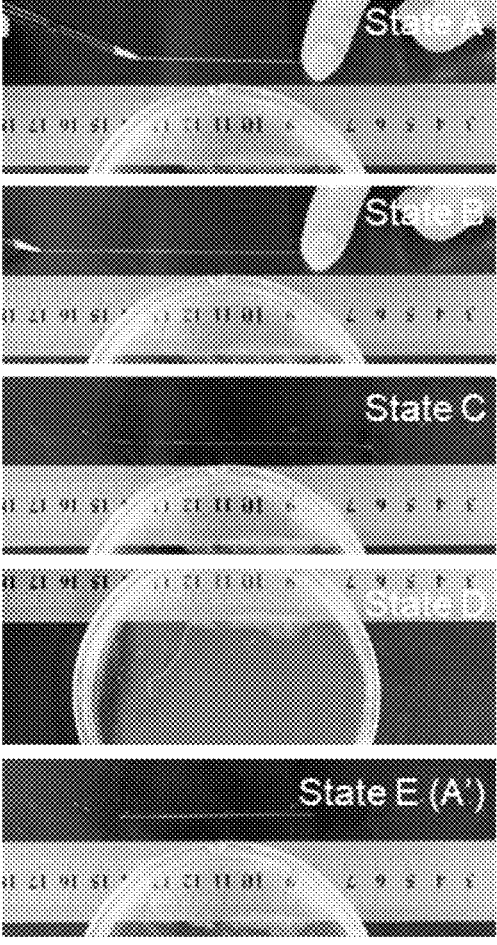
FIG. 4D illustrates the hydration-triggered shape-memory behavior of a single keratin fiber (state A is a wet at relaxed state; state B is a wet-stretching and drying under load; state C is dry after load removal; state D is a state of wet and recover; and state E, wet and fully relaxed after recovery)
Figure 4E:
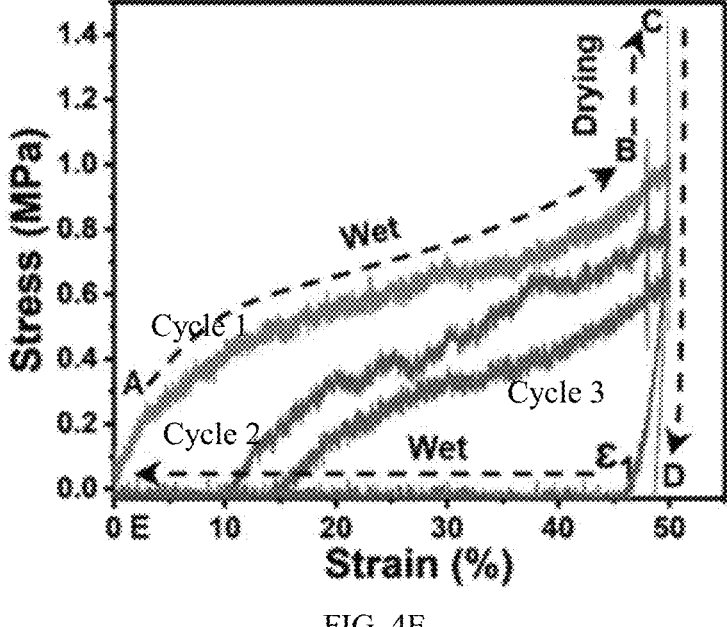
FIG. 4E shows a strain-stress plot of a single regenerated keratin fiber that undergoes multiple hydration-triggered shape-memory programming and recovery cycles.
Figure 4F:
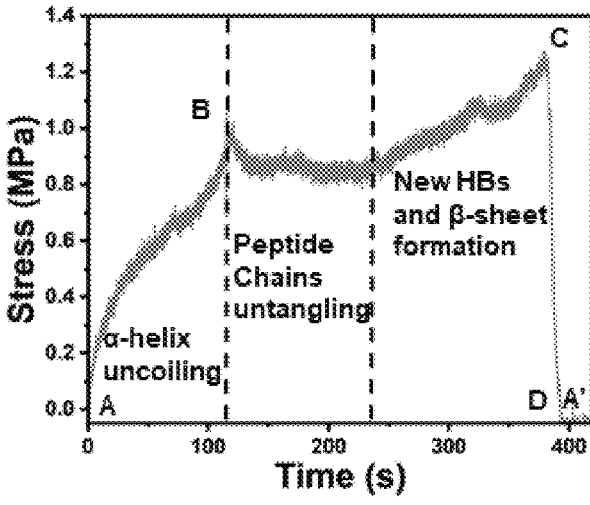
FIG. 4F depicts a time-stress plot of the full cycle obtained from the plot illustrated in FIG. 4E, FIG. 4G demonstrates shape-fixity ratio and shape-recovery rate determined from the strain-stress plot illustrated in FIG. 4E.
Figure 4G:
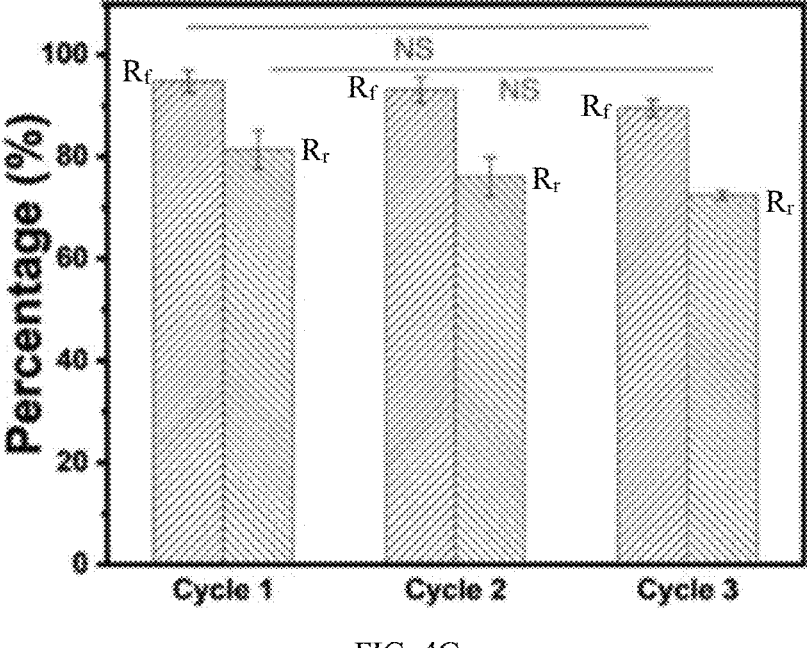
Figure 4H:
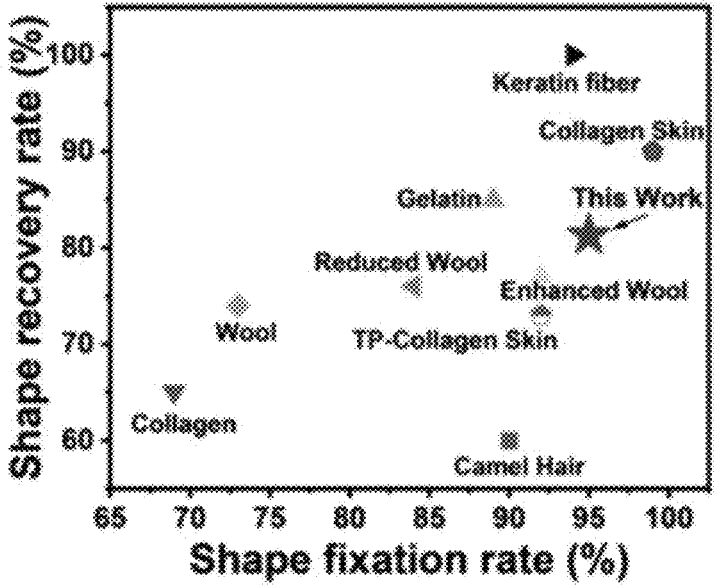
FIG. 4H depicts the summary and comparison of the shape-memory performance among the keratin fibers investigated in the present invention and other protein-based shape-memory materials.

The water-triggered shape-memory effect of a single keratin fiber is demonstrated in FIG. 4D. A single keratin fiber is wetted in deionized water for a few seconds (state A), stretched manually in the wet state (state B), and then kept under loading in the air for 40 seconds to dry the fiber (state C). No visible shrinkage in length is observed after unloading. When the dried fiber is rewetted with deionized water (state D), it shrinks back to its original length within a few seconds (state E). The ability of the keratin fibers to recover their original length through hydration is quantified using a tensile test. Compared to the tensile plot in the dry state, the strain-stress curves in the wet state exhibit a more gradual transition among the elastic yield regions (FIG. 4E). During the holding and drying processes, the stress continues to increase, indicating the reformation of chemical bonds and β-sheets. The conformational transformation occurs during axial stretching in a wet state, as illustrated by the time-stress curves of the tensile test on a single regenerated keratin fiber (FIG. 4F). Tensile stress steadily increases as the strain increases, due to the formation of new hydrogen bonds and β-sheets. The cycle tensile test reveals that the shape-fixity ratio, indicating the ability to maintain the programmed shape, is 94.8±2.15%. The total shape-recovery rate, quantifying the ability to recover the original shape after N cycles, is determined to be 81.4±3.84% (FIG. 4G). Although the mean value of the shape-recovery rate decreases slightly after the cycle test, no significant difference is observed, indicating the stability and favorable mechanical properties of the keratin fiber. The slight decrement can be avoided when tested in water. The shape-memory performance of the regenerated keratin fibers is comparable to that of other protein-based shape-memory materials, as shown in FIG. 4H.

Figure 4I:
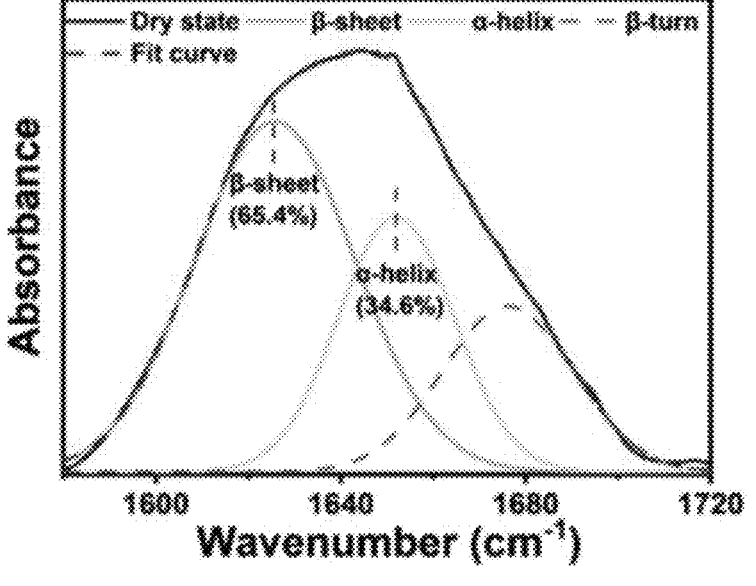
FIG. 4I and FIG. 4J show the amide I region obtained from FTIR spectrum deconvolution analysis of keratin fibers under dry conditions (FIG. 4I) and wet conditions (FIG. 4J)
Figure 4J:
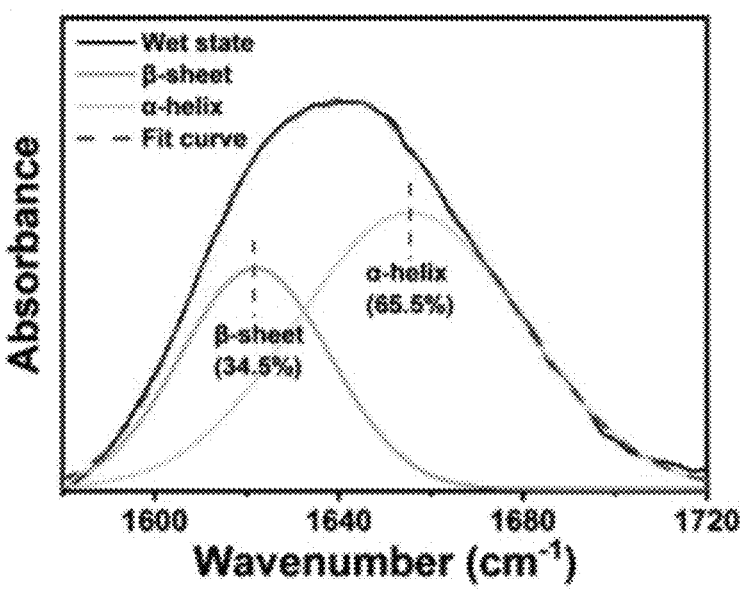
Figure 4K:
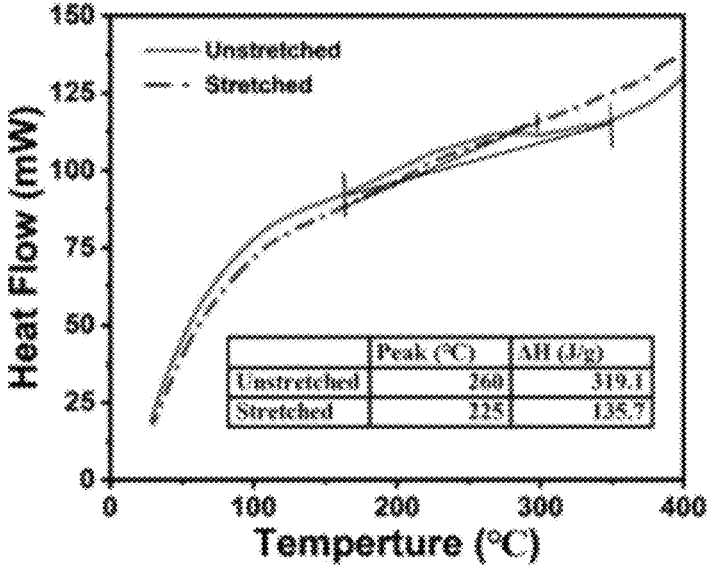
FIG. 4K depicts the DSC curves of keratin fibers before and after stretching.
Figure 4L:
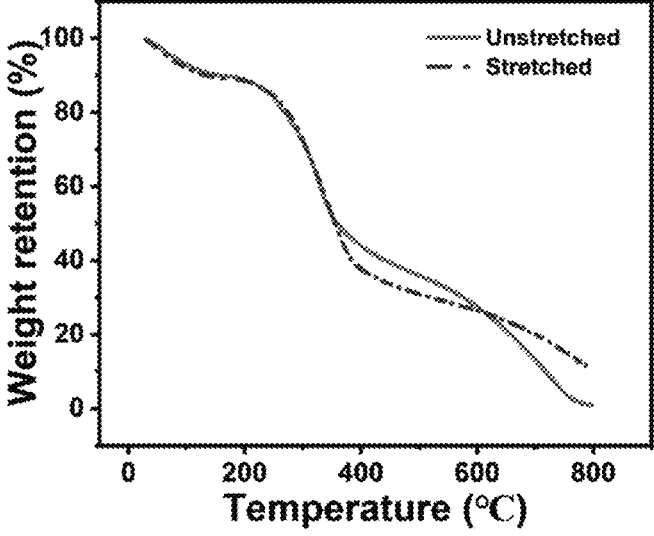
FIG. 4L shows the TGA curves of unstretched and stretched keratin fibers.
Figure 4M:
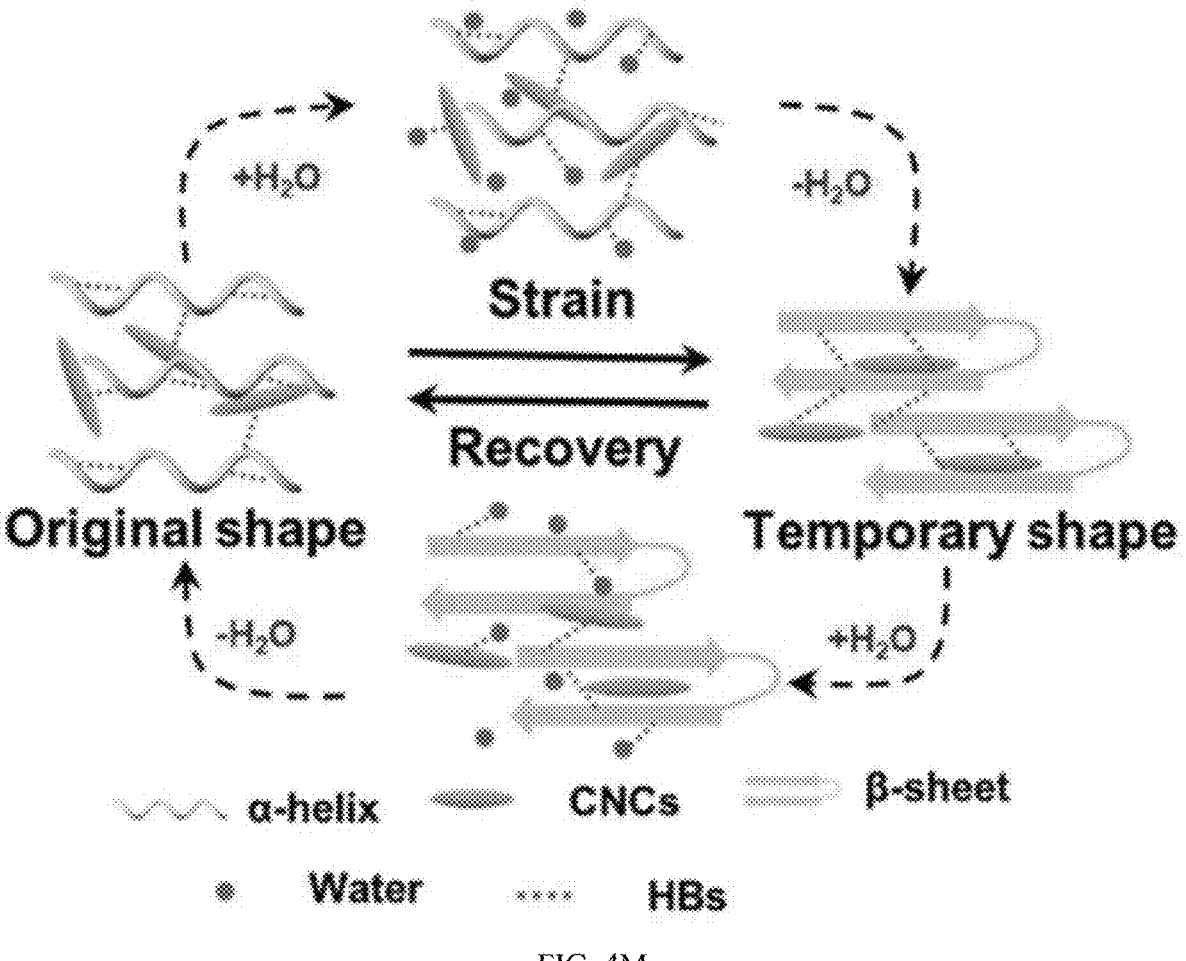
FIG. 4M depicts the reconfiguration of protein secondary structures triggered by strain and water.
Figure 4N:
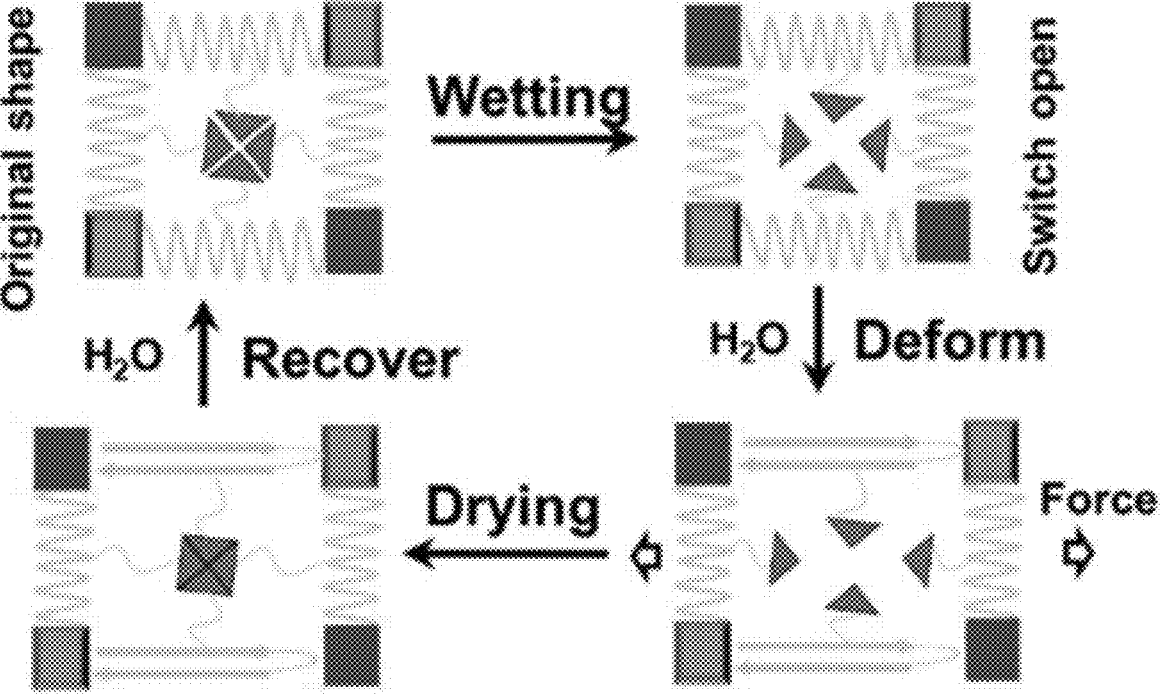

Furthermore, the mechanism of the conformational shift from α-helix to β-sheet during various shape-memory programming phases is confirmed by analyzing the deconvolution of the amide I FTIR spectrum (FIG. 4I and FIG. 4J), which shows a higher content of α-helix/random coil after hydration. The strain-induced conformational change is also demonstrated by the differential scanning calorimetry (DSC) curves (FIG. 4K), which exhibits a smaller melting enthalpy after stretching, and the thermogravimetric analysis (TGA) curves (FIG. 4L), which show less weight loss of the stretched fiber. Therefore, the mechanism of shape-memory fibers can be explained as a reversible change in the protein secondary structure upon hydration and axial force (FIG. 4M). This is further illustrated using the net-point model (FIG. 4N), in which hydrogen bonds function as switches triggered by water to ensure the mobility and fixation of keratin molecules, while disulfide bonds and CNCs act as cross-linking points to maintain both the original and temporary shapes.

Figure 5A:
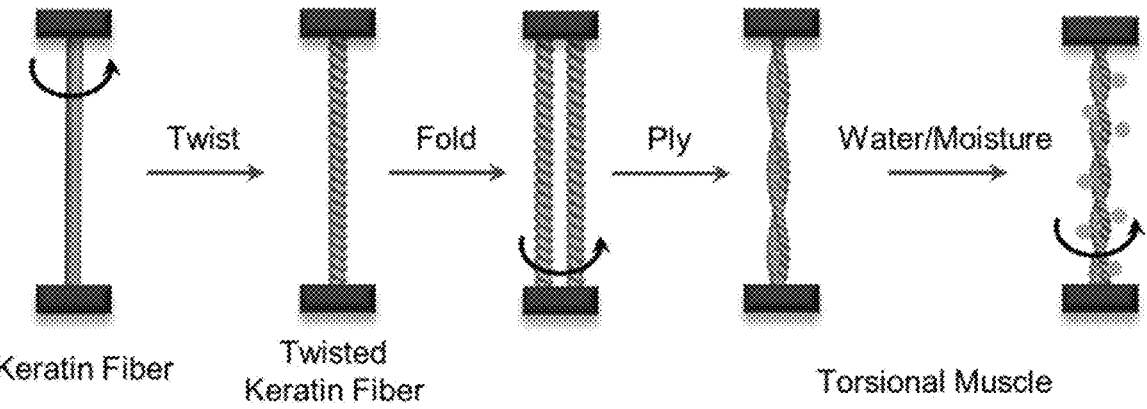
Figure 5B:
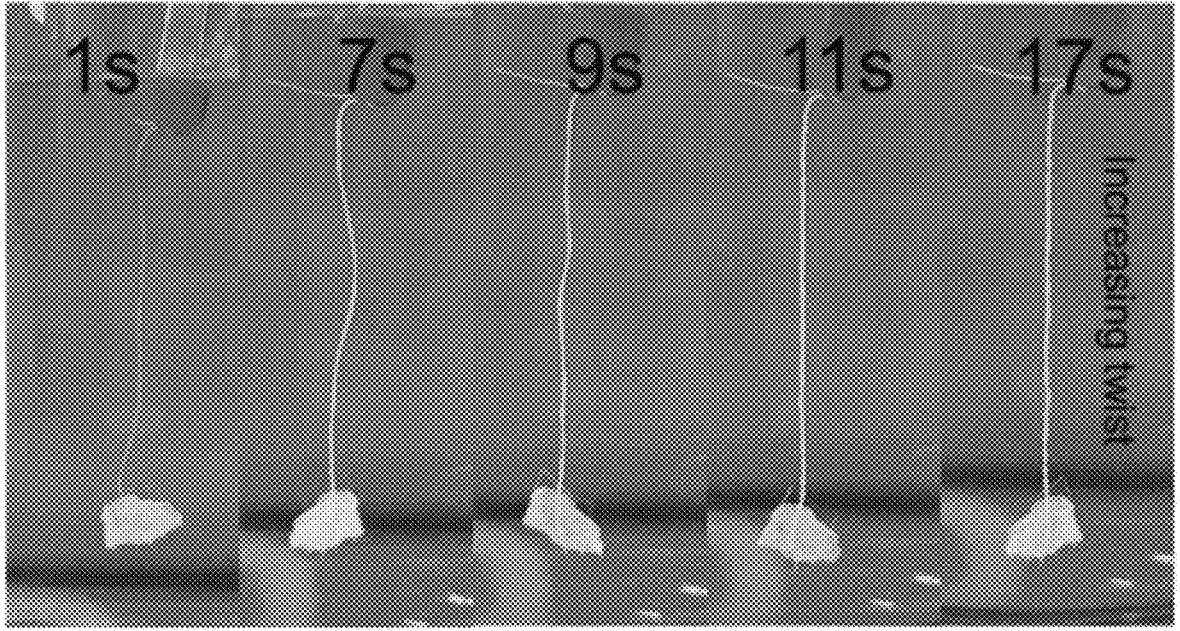

Example 4. Humidity/Hydration-Sensitive Textile Actuator Adopting the Hydration-Responsive Shape-Memory Keratin Fibers Building on their intrinsic shape-memory properties that originate from their reversible secondary structure, natural protein-based fibers such as wool, hair, and silk have been used as textile artificial muscles by constructing hierarchical textile structures from fiber to ply yarn. Considering the water-triggered shape-memory characteristics of keratin fibers, it has been utilized as hydration-sensitive textile actuators. Keratin artificial muscles can be fabricated by inserting a twist into the fiber. As shown in FIG. 5A, a single keratin fiber is first wetted in deionized water and twisted in the wet state. After folding the fibers, a ply yarn structure is obtained. When the ply yarn is placed in water, it acts as a torsional muscle that self-rotated due to self-twisting. As demonstrated in FIG. 5B, a glass paddle is rotated, driven by the torsional muscle's hydration responsiveness. This procedure showcases the potential of keratin fibers for use in humidity/hydration-sensitive artificial muscles.

Figure 5C:
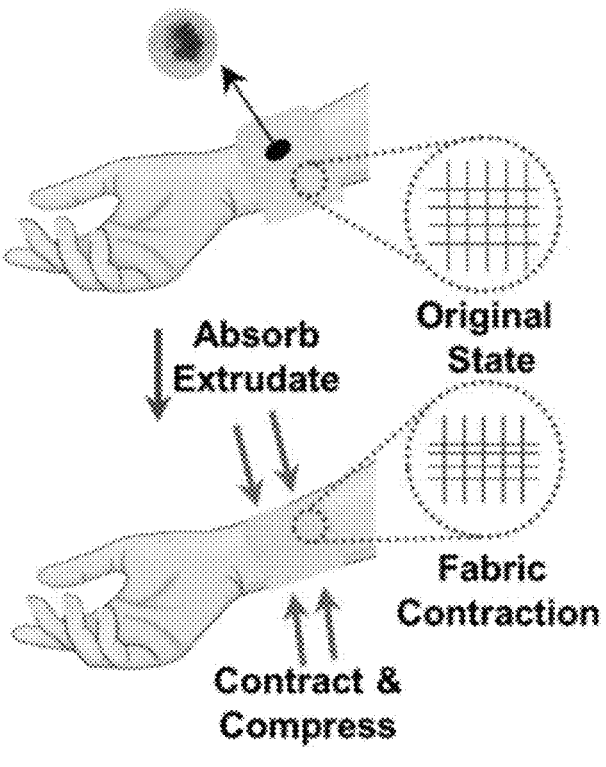

The keratin fibers can be manipulated and processed into woven fabrics. Additionally, their hydration responsiveness makes them potential candidates for smart textiles for thermal management, humidity-sensitive windows, and humidity indicators. Furthermore, due to their biocompatibility and biodegradability, they hold promise for biomedical devices, such as wound dressings, as illustrated conceptually in FIG. 5C. Smart bandages made from these fibers can absorb wound exudate and contract to better fit the wound. Moreover, the force generated by fiber contraction is beneficial for wound healing when compression therapy is needed. Thus, regenerated shape-memory keratin fibers show great potential across various application fields.

In summary, the present invention provides a green and cost-effective approach for spinning keratin fibers at low spinning dope concentrations by adding a small amount of CNCs. This addition enables the formation of β-sheet conformation and improves the viscoelasticity of the spinning dope. The regenerated keratin fibers exhibit a favorable water-triggered shape-memory effect, with a shape-fixity ratio of 94.8±2.15% and a shape-recovery rate of 81.4±3.84%, comparable to other protein-based shape-memory materials. Due to the preservation of the keratin molecular backbone, restoration of protein secondary structure, and enhancement effects of CNCs, the keratin fibers show excellent mechanical performance with wet-extensibility up to 360%.

The underlying mechanism of this shape-memory feature is investigated and elaborated. Keratin fibers demonstrate potential in the manufacture of macroscopic yarns and textile actuators. Their inherent biocompatibility and biodegradability make them viable substitutes for petroleum-based polymers in engineering strain-responsive and hydration-sensitive textiles, allowing applications in the biomedical field. It is also practicable that multifunctional and multi-stimuli-sensitive keratin-based fibers can be achieved by incorporating functional polymers or nanoparticles into the keratin system.

As used herein and not otherwise defined, the terms "substantially," "substantial," "approximately" and "about" are used to describe and account for small variations. When used in conjunction with an event or circumstance, the terms can encompass instances in which the event or circumstance occurs precisely as well as instances in which the event or circumstance occurs to a close approximation. For example, when used in conjunction with a numerical value, the terms can encompass a range of variation of less than or equal to $\pm10\%$ of that numerical value, such as less than or equal to $\pm5\%$, less than or equal to $\pm4\%$, less than or equal to $\pm3\%$, less than or equal to $\pm2\%$, less than or equal to $\pm1\%$, less than or equal to $\pm0.5\%$, less than or equal to $\pm0.1\%$, or less than or equal to $\pm0.05\%$.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated.

The invention claimed is:

1. A method of fabricating a hydration-responsive shape-memory keratin composite fiber, comprising:
   conducting a reduction reaction on a keratin source for extracting keratin molecules utilizing L-cysteine and urea;
   mixing the extracted keratin molecules, cellulose nanocrystals (CNCs) and a reducing agent in an alkaline solution to obtain a homogenous keratin spinning dope;
   extruding the keratin spinning dope through a needle by a pump to a coagulation bath to form as-spun fibers;
   oxidizing the as-spun fibers to generate disulfide bonds between α-helix subunits to form keratin α-helices; and
   crosslinking the keratin α-helices to form hydration-responsive shape-memory keratin composite fibers.

2. The method of claim 1, wherein the extruding is performed with an extrusion speed of 0.8-1 mL/h.

3. The method of claim 1, wherein the keratin source comprises wool, feathers, horns, hooves, mammalian hair, mammalian skin, mammalian nails and mammalian claws.

4. The method of claim 1, wherein the coagulation bath is a sodium dihydrogen phosphate aqueous solution.

5. The method of claim 4, wherein the coagulation bath has a pH less than 4.3 to facilitate keratin solidification and ion diffusion.

6. The method of claim 1, wherein the crosslinking is utilizing glutaraldehyde as a crosslinker.

* * * * *